US012647700B2

(12) United States Patent
Yabe

(10) Patent No.: US 12,647,700 B2
(45) Date of Patent: Jun. 2, 2026

(54) CONTROL DEVICE, ENDOSCOPE APPARATUS, AND CONTROL METHOD

(71) Applicant: OLYMPUS MEDICAL SYSTEMS CORP., Tokyo (JP)

(72) Inventor: Yusuke Yabe, Chofu (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 323 days.

(21) Appl. No.: 18/367,061

(22) Filed: Sep. 12, 2023

(65) Prior Publication Data

US 2023/0421928 A1     Dec. 28, 2023

Related U.S. Application Data

(63) Continuation of application No. PCT/JP2021/010725, filed on Mar. 17, 2021.

(51) Int. Cl.
*H04N 25/78*          (2023.01)
*A61B 1/00*          (2006.01)
(Continued)

(52) U.S. Cl.
CPC ......... *H04N 25/78* (2023.01); *A61B 1/00009* (2013.01); *A61B 1/0655* (2022.02); *H04N 25/706* (2023.01)

(58) Field of Classification Search
CPC .... H04N 25/78; H04N 25/706; H04N 23/555; H04N 23/56; A61B 1/00009;
(Continued)

(56) References Cited

U.S. PATENT DOCUMENTS

2013/0030268 A1     1/2013 Saito
2015/0094531 A1*    4/2015 Ishimaru .............. A61B 1/0655
                                                                    600/103
(Continued)

FOREIGN PATENT DOCUMENTS

JP          2011-206336 A     10/2011
JP          2013-022341 A     2/2013
(Continued)

OTHER PUBLICATIONS

International Search Report dated Jun. 8, 2021 received in PCT/JP2021/010725.

*Primary Examiner* — Nhan T Tran
(74) *Attorney, Agent, or Firm* — Scully, Scott, Murphy & Presser, P.C.

(57) ABSTRACT

A control device includes a processor. The processor controls an image sensor to read out first imaging signals in a first readout period, the first imaging signals being signals from a first quantity of pixels, and read out second imaging signals in a second readout period, the second imaging signals being signals from a second quantity of pixels, the second quantity being smaller than the first quantity, the second readout period being shorter than the first readout period. The processor controls a light source to emit first illumination light in a first exposure period before the first readout period, and emit second illumination light in a second exposure period before the second readout period. The processor generates a display image from the first imaging signals. The processor generates a support image from the second imaging signals. The processor generates support information based on the support image.

14 Claims, 22 Drawing Sheets

(51) Int. Cl.
    *A61B 1/06*        (2006.01)
    *H04N 25/706*    (2023.01)

(58) Field of Classification Search
    CPC ... A61B 1/0655; A61B 1/00006; A61B 1/045;
                              A61B 1/0638
    See application file for complete search history.

(56)                 References Cited

U.S. PATENT DOCUMENTS

| | | | |
|---|---|---|---|
| 2016/0353972 A1* | 12/2016 | Yano | A61B 1/000094 |
| 2018/0227476 A1* | 8/2018 | Kobayashi | H04N 25/531 |
| 2019/0320877 A1* | 10/2019 | Sakai | A61B 1/063 |
| 2021/0385367 A1 | 12/2021 | Yabe | |
| 2023/0319386 A1* | 10/2023 | Hayashi | H04N 23/73 |
| | | | 348/68 |

FOREIGN PATENT DOCUMENTS

| | | | |
|---|---|---|---|
| JP | 2019-191321 A | 10/2019 |
| WO | 2015/136963 A1 | 9/2015 |
| WO | 2020/174572 A1 | 9/2020 |

* cited by examiner

FIG.10

PRESENCE DIAGNOSIS MODE

QUALITATIVE DIAGNOSIS MODE

CONTROL DEVICE, ENDOSCOPE APPARATUS, AND CONTROL METHOD

CROSS REFERENCE TO RELATED APPLICATIONS

This application is a continuation of International Patent Application No. PCT/JP2021/010725, having an international filing date of Mar. 17, 2021, which designated the United States, the entirety of which is incorporated herein by reference.

BACKGROUND OF THE INVENTION

An endoscope apparatus that comes with a diagnosis support function is known. Examples of diagnosis support include a function of extracting a lesional portion from an image with artificial intelligence (AI) and presenting the lesional portion. For example, International Publication No. 2020/174572 proposes an endoscope apparatus that is capable of individually observing an image to be used for display and an image to be used for extraction of support information in order to present highly accurate support information.

SUMMARY OF THE INVENTION

In accordance with one of some aspect, there is provided a control device comprising
a processor configured to:
control an image sensor including a plurality of pixels to
read out first imaging signals in a first readout period, the first imaging signals being signals from a first quantity of pixels included in the plurality of pixels, the first readout period being a period for readout of the signals from the first quantity of pixels, and
read out second imaging signals in a second readout period, the second imaging signals being signals from a second quantity of pixels included in the plurality of pixels, the second readout period being a period for readout of the signals from the second quantity of pixels and being shorter than the first readout period, the second quantity being smaller than the first quantity;
control a light source that emits illumination light toward an object to
emit first illumination light in a first exposure period before the first readout period, and
emit second illumination light in a second exposure period before the second readout period;
generate a display image from the first imaging signals obtained by imaging of the object illuminated with the first illumination light;
generate a support image from the second imaging signals obtained by imaging of the object illuminated with the second illumination light; and
generate support information to support diagnosis or treatment based on the support image.
In accordance with one of some aspect, there is provided an endoscope apparatus comprising:
an image sensor including a plurality of pixels;
a light source that emits illumination light toward an object; and
a processor configured to
control the image sensor to
read out first imaging signals in a first readout period, the first imaging signals being signals from a first quantity of pixels included in the plurality of pixels, the first readout period being a period for readout of the signals from the first quantity of pixels, and
read out second imaging signals in a second readout period, the second imaging signals being signals from a second quantity of pixels included in the plurality of pixels, the second readout period being a period for readout of the signals from the second quantity of pixels and being shorter than the first readout period, the second quantity being smaller than the first quantity,
control the light source to
emit first illumination light in a first exposure period before the first readout period, and
emit second illumination light in a second exposure period before the second readout period,
generate a display image from the first imaging signals obtained by imaging of the object illuminated with first illumination light,
generate a support image from the second imaging signals obtained by imaging of the object illuminated with the second illumination light, and
generate support information to support diagnosis or treatment based on the support image.
In accordance with one of some aspect, there is provided a control method for an endoscope apparatus, comprising:
controlling an image sensor including a plurality of pixels to
read out first imaging signals in a first readout period, the first imaging signals being signals from a first quantity of pixels included in the plurality of pixels, the first readout period being a period for readout of the signals from the first quantity of pixels, and
read out second imaging signals in a second readout period, the second imaging signals being signals from a second quantity of pixels included in the plurality of pixels, the second readout period being a period for readout of the signals from the second quantity of pixels and being shorter than the first readout period, the second quantity being smaller than the first quantity;
controlling a light source that emits illumination light toward an object to
emit first illumination light in a first exposure period before the first readout period, and
emit second illumination light in a second exposure period before the second readout period;
generating a display image from the first imaging signals obtained by imaging of the object illuminated with the first illumination light;
generating a support image from the second imaging signals obtained by imaging of the object illuminated with the second illumination light; and
generating support information to support diagnosis or treatment based on the support image.

BRIEF DESCRIPTION OF THE DRAWINGS

FIG. 10 is a diagram for explaining a generation process of generating a display image.

DETAILED DESCRIPTION

Figure 1:
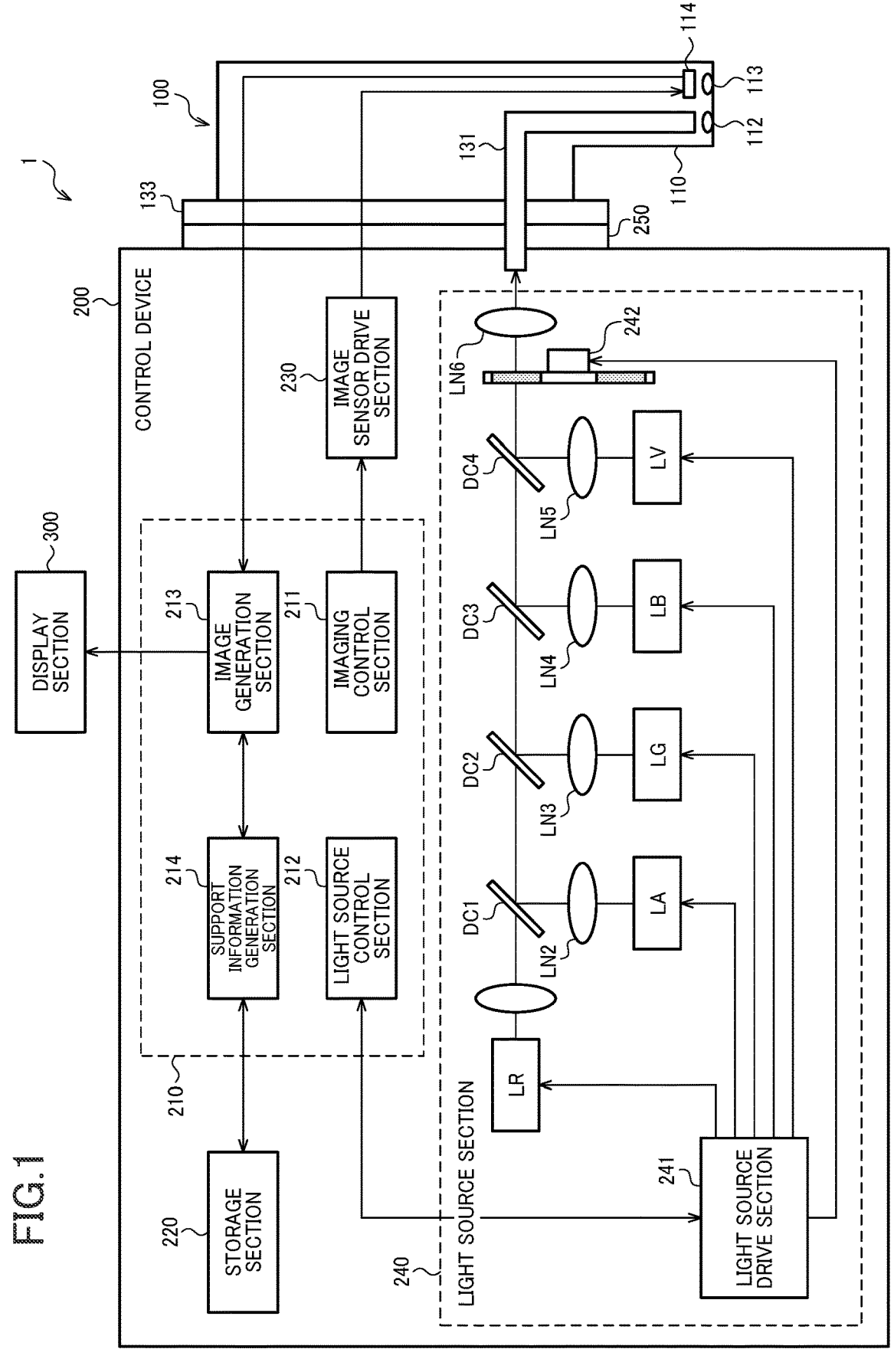
FIG. 1 shows a first configuration example of an endoscope apparatus.

The following disclosure provides many different embodiments, or examples, for implementing different features of the provided subject matter. These are, of course, merely examples and are not intended to be limiting. In addition, the disclosure may repeat reference numerals and/ or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

For example, the following description is given of a case where a control device is applied to an endoscope apparatus, but the control device according to the present disclosure can be applied to various apparatuses that acquire images using a rolling shutter-type image sensor.

1. First Configuration Example of Endoscope Apparatus

First, a configuration of an endoscope apparatus 1 according to the present embodiment is described. Thereafter, a method of extending an exposure period in which a display image is captured will be described.

FIG. 1 shows a first configuration example of the endoscope apparatus 1. As shown in FIG. 1, the endoscope apparatus 1 includes an endoscope 100, a control device 200, and a display section 300. Note that the endoscope 100 is also referred to as a scope, and the display section 300 is also referred to as a display or a display device. Note that FIG. 1 mainly shows portions necessary for explanation about the present embodiment, and omits details other than the necessary portions as appropriate.

The endoscope 100 includes an insertion section 110 and a connector 133. The insertion section 110 has flexibility, and can be inserted into a body cavity of a living body. The body cavity of the living body is an object in the present embodiment. The connector 133 is arranged at one end of the endoscope 100, and can be attached/detached to/from a connector 250 on the control device 200 side. The connector 133 and the connector 250 are connected to each other, whereby the endoscope 100 and the control device 200 are electrically and optically connected to each other.

At a leading end of the insertion section 110, arranged are an illumination optical system 112 that emits illumination light toward the object and an imaging device that receives illumination light reflected or scattered on a surface of the object to capture an image. The insertion section 110 includes a light guide 131 that guides illumination light emitted from a light source section 240 to the illumination optical system 112.

The illumination optical system 112 broadens illumination light guided by the light guide 131 to have a desired radiation angle. While one illumination lens is arranged at the leading end of the insertion section 110 in FIG. 1, a plurality of illumination lenses may be arranged at the leading end of the insertion section 110. The light guide 131 is, for example, an optical fiber bundle. The imaging device includes an objective optical system 113 that forms an image of the object and an image sensor 114 that captures an object image formed by the objective optical system 113. The image sensor 114 is a complementary metal oxide semiconductor (CMOS) image sensor, and is driven by an image sensor drive section 230 to output imaging signals to the control device 200. The image sensor drive section 230 will be described later.

The image sensor 114 receives light from the object illuminated with light generated by the light source section 240 and generates electric signals. The image sensor 114 includes a light receiving section, which includes a plurality of horizontal scanning lines. Each horizontal scanning line includes a plurality of pixels. The image sensor 114 is a rolling shutter-type image sensor. That is, the image sensor 114 sequentially reads out electric signals on a horizontal scanning line-by-horizontal scanning line basis, and starts to sequentially expose the horizontal scanning lines from a horizontal scanning line from which readout of electric signals has been completed to generate imaging signals for one frame.

Figure 2:
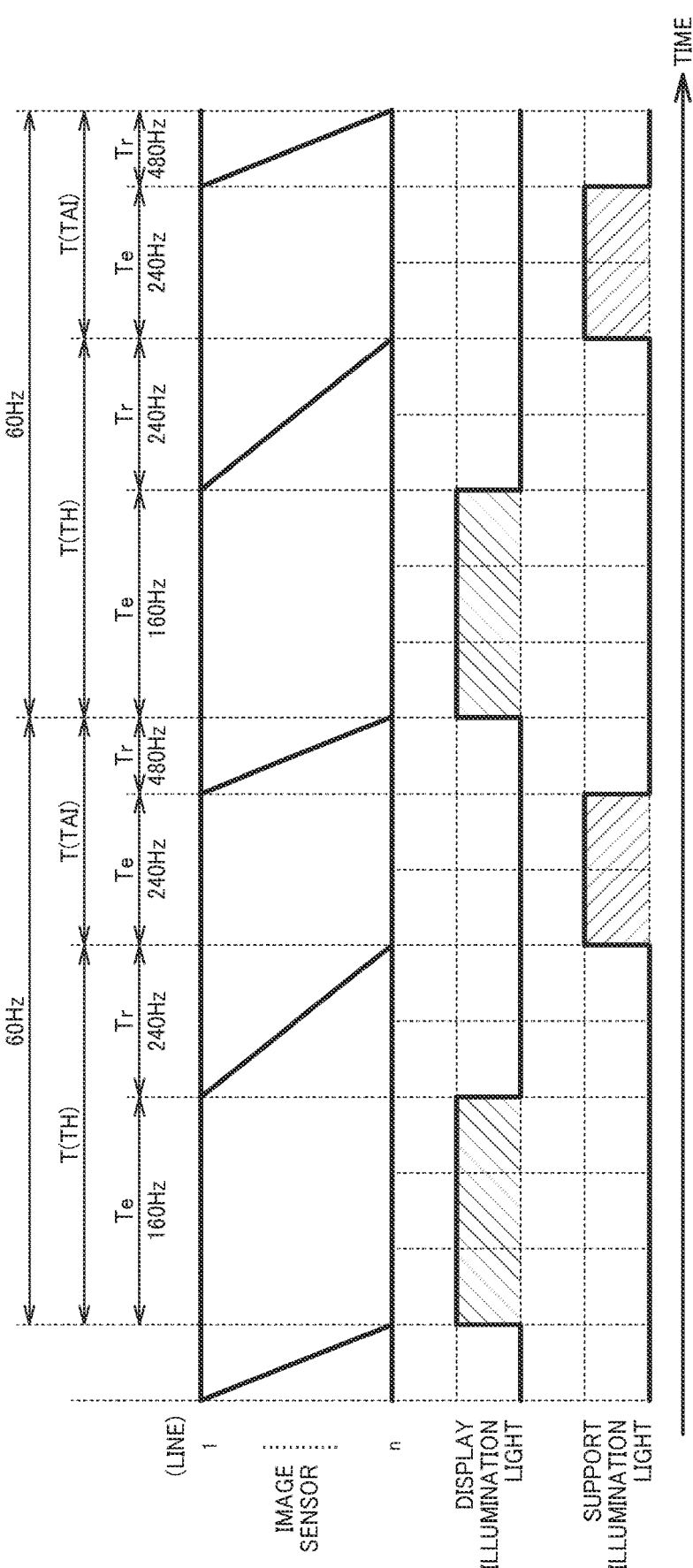
FIG. 2 is a chart showing a light emission sequence and an imaging sequence according to a first embodiment.

As shown in FIG. 2, assume that the image sensor 114 includes the first to n-th horizontal scanning lines. The first horizontal scanning line is a horizontal scanning line in the first row, and the n-th horizontal scanning line is a horizontal scanning line in the final row, where n is a natural number of 2 or more. The first to n-th horizontal scanning lines sequentially serve as readout lines, and pixel signals are read out therefrom. Hence, there generates a time difference in readout timing between the line in the first row and the line in the n-th row.

A period after the start of readout of pixel data of the first horizontal scanning line of the image sensor 114 until the end of readout of pixel data of the n-th horizontal scanning line is a video image readout period Tr of a CMOS rolling shutter. A period that is a period excluding the video image readout period Tr occurring on a periodic basis and in which all the lines are simultaneously exposed is an all-line simultaneous exposure period Te of the CMOS rolling shutter. The video image readout period Tr and the all-line simultaneous exposure period Te are included in a period T for one field or one frame of the image (one cycle of the CMOS rolling shutter). Note that details of FIG. 2 will be described later.

Note that the insertion section 110 can come with various functions or mechanisms that are not shown. For example, a scope operation section for operating the endoscope 100, a curve mechanism for curving the leading end section, a forceps hole into which a forceps or the like can be inserted, a treatment tool such as an electrosurgical knife to be used for treatment, an air supply/water supply tube that enables jetting and suction of liquid and gas, or the like can be mounted on the insertion section 110. Part of the components included in the insertion section 110 may be omitted.

The control device 200 performs control of each section of the endoscope apparatus 1 and an image process on an image captured by the endoscope 100. The control device 200 includes the light source section 240, a control section 210, an image sensor drive section 230, a storage section 220, and the connector 250. The light source section 240 is also referred to as a light source device. The control section 210 is also referred to as a control circuit. The image sensor drive section 230 is also referred to as an image sensor drive circuit. The storage section 220 is also referred to as a storage device.

The control section 210 controls the whole or each section of the endoscope apparatus 1. The control section 210 includes an imaging control section 211, a light source control section 212, an image generation section 213, and a support information generation section 214. Various kinds of hardware that implements the control section 210 can be assumed. For example, the control device 200 includes a processor and a memory that stores a program. Part or all of functions of the control section 210 are described in the program. The processor executes the program stored in the memory and thereby executes part or all of the functions of the control section 210 as a process. The processor may be a central processing unit (CPU), a microprocessing unit (MPU), a digital signal processor (DSP), or the like, or may alternatively be an application-specific integrated circuit (ASIC), a field-programmable gate array (FPGA), or the like. The memory may be a semiconductor memory such as a random-access memory (RAM) and a nonvolatile memory, or may alternatively be a magnetic storage device such as a hard disk drive. Functions of the imaging control section 211, the light source control section 212, the image generation section 213, and the support information generation section 214 are described in the program. Alternatively, functions of the imaging control section 211, the light source control section 212, the image generation section 213, or the support information generation section 214, or functions of two or three of these sections may be described in the program. The program according to the present embodiment may be stored in an information storage medium. The information storage medium is a computer readable medium. As the information storage medium, various kinds of media can be assumed, such as an optical disk such as a digital versatile disk (DVD) and a compact disk (CD), a hard disk, and a semiconductor memory such as a nonvolatile memory and a read-only memory (ROM).

The imaging control section 211 controls the image sensor drive section 230 to control exposure of the image sensor 114 and readout of a signal. Specifically, the imaging control section 211 controls the start and end of exposure of each horizontal scanning line according to the rolling shutter method and readout of imaging signals from each horizontal scanning line.

The light source control section 212 controls spectral characteristics of illumination light emitted from the light source section 240. That is, the light source control section 212 outputs a control signal to the light source drive section 241, and thereby emits light or turns off light from each light source or controls a light emission quantity of each light source. In addition, the light source control section 212 controls a filter section 242 of the light source section 240 to control spectral characteristics of illumination light. The light source control section 212 follows a predetermined light emission sequence to control a light emission timing of each light source. The light source control section 212 performs the above-mentioned control of the light source section 240 to emit display illumination light and support illumination light in a time-division manner.

The image generation section 213 generates a display image based on imaging signals from the image sensor 114. Specifically, the image generation section 213 generates the display image from imaging signals obtained by imaging performed when the display illumination light is emitted toward the object. Furthermore, the image generation section 213 generates the support image from imaging signals obtained by imaging performed when the support illumination light is emitted toward the object. The image generation section 213 performs, for example, an image process such as a process of generating a red, green, and blue (RGB) image by subjecting imaging signals to an interpolation process, a white balance process, or a grayscale transformation process. In addition, the image generation section 213 superimposes a display content based on support information generated by the support information generation section 214 on a display image, and outputs the display image to the display section 300. The support information generation section 214 will be described later.

The display section 300 is, for example, a display device such as a liquid crystal display. The display section 300 displays the display image output from the image generation section 213. With this configuration, the image captured with the display illumination light and the support information superimposed on the image are presented to a user of the endoscope apparatus 1.

The support information generation section 214 generates the support information from the support image. The support information is information to support diagnosis or treatment performed by a doctor who uses the endoscope apparatus 1. The support information generation section 214 performs an inference process with artificial intelligence (AI). That is, the support information generation section 214 performs the inference process from input image signals to extract the support information. As the AI, various kinds of image recognition methods or various kinds of machine learning methods can be adopted. The machine learning is a process of making various kinds of inference based on a result of training. There is a neural network as representative AI, but the AI is not limited thereto. Various kinds of known machine learning methods can be adopted as the AI in the present embodiment.

The storage section 220 is, for example, a semiconductor memory, or a storage device such as a hard disk drive. The storage section 220 stores information of a trained model. The support information generation section 214 performs the inference process with the above-mentioned AI based on the trained model. Various kinds of hardware for the support information generation section 214 that executes the inference process can be assumed. The support information generation section 214 is, for example, a general purpose processor such as a CPU. In this case, the storage section 220 stores a program in which an inference algorithm is described, and a parameter used in the inference algorithm as the information of the trained model. Alternatively, the support information generation section 214 may be a dedicated processor that implements the inference algorithm as hardware. In this case, the storage section 220 stores the parameter used in the inference algorithm as the information of the trained model.

The inference algorithm is the neural network. The neural network includes an input layer that takes input data, an intermediate layer that executes a calculation process based on data input via the input layer, and an output layer that outputs data based on a calculation result output from the intermediate layer. A node included in the input layer and a node included in the intermediate layer are connected to each other, and the node included in the intermediate layer and a node included in the output layer are connected to each other. A weight coefficient assigned between the connected nodes corresponds to the above-mentioned parameter.

The image sensor drive section 230 is a circuit that generates an image sensor drive signal based on an image sensor control signal from the imaging control section 211, and that drives the image sensor 114. The image sensor drive signal includes a synchronization signal that gives an exposure timing and a readout timing to the image sensor 114. In addition, the image sensor drive section 230 is a circuit that generates an electronic shutter drive signal based on an electronic shutter control signal from the imaging control section 211 and that performs an electronic shutter process of the image sensor 114.

The light source section 240 generates illumination light and causes the illumination light to be incident on the light guide 131. The light source section 240 is capable of generating illumination light having various kinds of spectral characteristics, and emits the display illumination light for capturing the display image and the support illumination light for generating the support information in a time-division manner Specifically, the light source section 240 includes a light source LR that emits red light, a light source LA that emits amber light, a light source LG that emits green light, a light source LB that emits blue light, a light source LV that emits purple light, lenses LN1 to LN6, dichroic mirrors DC1 to DC4, a light source drive section 241, and the filter section 242. A configuration of the light source section 240 is not limited to the configuration shown in FIG. 1. For example, an optical multiplexing section including an optical fiber may be arranged in substitution for the dichroic mirrors DC1 to DC4.

Each of the light sources LR, LA, LG, LB, and LV is a semiconductor laser (laser diode). In this case, the illumination light is laser light. Alternatively, each of the light sources LR, LA, LG, LB, and LV may be a light emitting diode (LED). For example, an LED that emits narrowband light with a wavelength band of several tens of nanometers can be adopted. However, the illumination light is not limited to the narrowband light, and for example, illumination light with a band appropriate for viewability of the display image or a method of extracting the support information is only required to be adopted.

The description will be given below taking a case where each of the light sources LR, LA, LG, LB, and LV is a semiconductor laser element as an example. The light source LR emits red laser light with a wavelength of $\lambda e=635$ nm. The light source LA emits orange laser light with a wavelength of $\lambda d=600$ nm. The light source LG emits green laser light with a wavelength of $\lambda c=532$ nm. The light source LB emits blue laser light with a wavelength of $\lambda b=445$ nm. The light source LV emits blue-violet laser light with a wavelength of $\lambda a=405$ nm. These types of light is, for example, narrowband light with a half-value width of several tens of nanometers. A quantity of light emitted from each light source is controlled independently. For example, an appropriate quantity of light according to viewability of the display image or the method of extracting the support information is only required to be adopted. Note that light emitted from each light source is not limited thereto. That is, the red light is only required to have a peak wavelength in a wavelength region of 615 to 680 nm; the amber light is only required to have a peak wavelength in a wavelength region of 586 to 615 nm; the green light is only required to have a peak wavelength in a wavelength region of 495 to 585 nm; the blue light is only required to have a peak wavelength in a wavelength region of 440 to 495 nm; and the blue-violet light is only required to have a peak wavelength in a wavelength region of 400 to 440 nm.

The light source drive section 241 is electrically connected to the light sources LR, LA, LG, LB, and LV. The light source drive section 241 is controlled by the light source control section 212, and drives the light sources LR, LA, LG, LB, and LV based on the control. The light sources LR, LA, LG, LB, and LV oscillate laser light using power supplied from the light source drive section 241.

The lens LN1 causes light emitted from the light source LR to be incident on the dichroic mirror DC1. Similarly, the lenses LN2, LN3, LN4, and LN5 cause light emitted from the light sources LA, LG, LB, and LV, respectively, to be incident on the dichroic mirrors DC1, DC2, DC3, and DC4, respectively.

The dichroic mirror DC1 causes light emitted from the light source LR to passes therethrough, and reflects light emitted from the light source LA. Similarly, the dichroic mirrors DC2, DC3, and DC4 cause light coming from the dichroic mirrors DC1, DC2, and DC3, respectively, to pass therethrough, and reflect light emitted from the light sources LG, LB, and LV, respectively.

The filter section 242 has a configuration in which a filter and a passing portion are switchable. A plurality of filters may be arranged. The passing portion causes light coming from the dichroic mirror DC4 to pass therethrough without changing spectral characteristics. The filter has spectral transmittance characteristics, and causes light in a wavelength region corresponding to the spectral transmittance characteristics among light coming from the dichroic mirror DC4 to pass therethrough. The light sources LR, LA, LG, LB, and LV are configured so that freely selected one or more of the light sources LR, LA, LG, LB, and LV are capable of emitting light. A light source that is caused to emit light is selected from these five light sources and a filter of the filter section 242 is selected, whereby illumination light having desired spectral characteristics is obtained.

The lens LN6 emits light that passes through the filter section 242 toward an incident end of the light guide 131 of the endoscope 100 connected to the connector 250.

2. Light Emission Sequence and Imaging Sequence

An operation of the endoscope apparatus 1 according to the present embodiment is described. The endoscope apparatus 1 has a diagnosis support mode such as a presence diagnosis mode and a qualitative diagnosis mode. The diagnosis support mode is a mode to cause the display section 300 to display the display image obtained by adding the support information extracted from the support image captured with the support illumination light to a normal image captured with the display illumination light. Details of the support illumination light and the support information in the diagnosis support mode will be described later, and a light emission sequence and an imaging sequence in the diagnosis support mode are described here. The sequences in each of the first to third embodiments, which will be described below, can be combined with each of various kinds of diagnosis support modes, which will be described later.

FIG. 2 is a diagram showing a light emission sequence and an imaging sequence according to the first embodiment. The image sensor 114 performs imaging to generate a normal image in a period TH, and performs imaging to generate a diagnosis support image in a period TAI.

In a drive sequence of the image sensor 114, an exposure period Te in which the object is imaged and a readout period Tr in which imaging signals are read out are repeated. Each of the period TH and the period TAI includes the exposure period Te and the readout period Tr.

When the display image is displayed at a frame rate of 60 Hz, for example, the exposure period Te in the period TH is at 160 Hz, the readout period Tr in the period TH is at 240 Hz, the exposure period Te in the period TAI is at 240 Hz, and the readout period Tr in the period TAI is at 480 Hz. A length of each period is indicated here by a frequency. For example, when a length of the exposure period Te is indicated by time, $1/160$ Hz is 6.25 ms.

In the exposure period Te in the period TH, the light source control section 212 causes the light source section 240 to emit white light therefrom as the display illumination light. The white light is only required to be light that allows an image captured with the light to be visually recognized as a substantially white light image. For example, all of the light sources LR, LA, LG, LB, and LV may be caused to emit light in the exposure period Te, but the configuration is not limited thereto.

The image sensor 114 receives return light of the display illumination light emitted onto the object. The image sensor 114 sequentially reads out electric signals from all the pixels on a horizontal scanning line-by-horizontal scanning line basis in the readout period Tr in the period TH. The image sensor 114 outputs the readout imaging signals to the control device 200. In addition, in the image sensor 114, an accumulated electric charge of each pixel on the horizontal scanning lines from which readout of the imaging signals is completed is sequentially discharged. The image generation section 213 generates the normal image from the imaging signals obtained by imaging performed in the period TH. The normal image is a white light image. The example in which the display image is the white light image is described here, but the image captured as the display image in the period TH is not limited to the white light image.

In the exposure period Te in the period TAI, the light source control section 212 causes the light source section 240 to emit the support illumination light therefrom. The support illumination light is light that is different in spectrum from the display illumination light. That is, at least one of the light source to be caused to emit light or a quantity of light from each light source is different between the exposure period Te in the period TAI and the exposure period Te in the period TH. Details of the support illumination light will be described later.

The image sensor 114 receives return light of the support illumination light emitted onto the object. In the readout period Tr in the period TH, the image sensor 114 selects all of the first to n-th horizontal scanning lines, that is, n horizontal scanning lines, and reads out electric signals from pixels on the selected horizontal scanning lines. In contrast, in the readout period Tr in the period TAI, the image sensor 114 selects horizontal scanning lines that are fewer than the n horizontal scanning lines from the first to n-th horizontal scanning lines, and reads out electric signals from pixels on the selected horizontal scanning lines. In the example shown in FIG. 2, the image sensor 114 selects n/2 horizontal scanning lines in the readout period Tr in the period TAI. With this process, the length of the readout period Tr in the period TAI is ½ the length of the readout period Tr in the period TH.

The image sensor 114 outputs the readout imaging signals to the control device 200. In the image sensor 114, an electric charge accumulated in each pixel on the horizontal scanning line from which readout of the imaging signals is completed and an electric charge accumulated in each pixel on horizontal scanning line that is skipped without being subjected to readout of imaging signals are sequentially discharged.

In the above-mentioned International Publication No. 2020/174572, all of the exposure period Te in the period TH, the readout period Tr in the period TH, the exposure period Te in the period TAI, and the readout period Tr in the period TAI are at 240 Hz. In the present embodiment, the readout period Tr in the period TH is at 480 Hz, and is half the length of the readout period Tr in the period TH according to International Publication No. 2020/174572. It is possible to extend the exposure period Te in the period TH by a reduction of the readout period Tr in the period TH. The exposure period Te in the period TH is at 160 Hz in the present embodiment in contrast with 240 Hz according to International Publication No. 2020/174572, and the length thereof is 1.5 times the length according to International Publication No. 2020/174572. This can extend the exposure period of the normal image serving as the display image in comparison with that in the related art.

Figure 3:
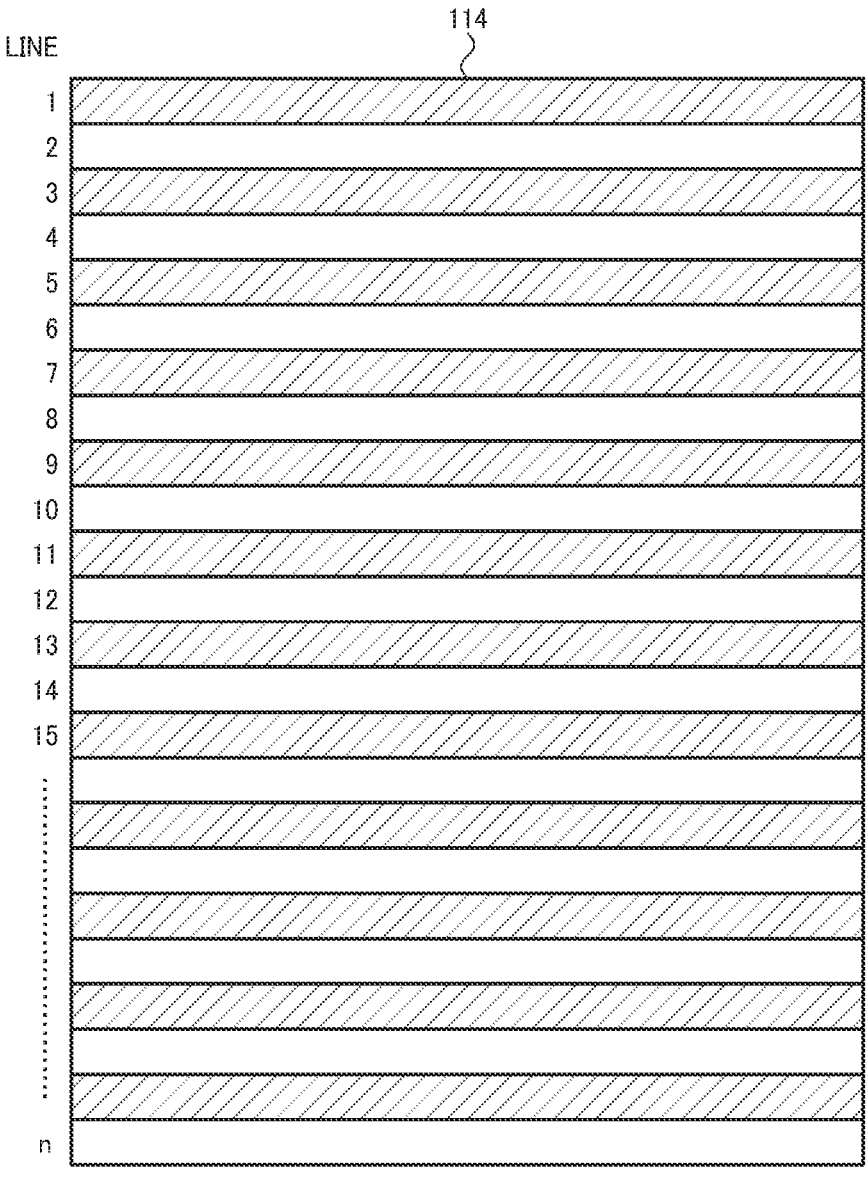
FIG. 3 is a diagram for explaining decimation readout according to a second embodiment.
Figure 4:
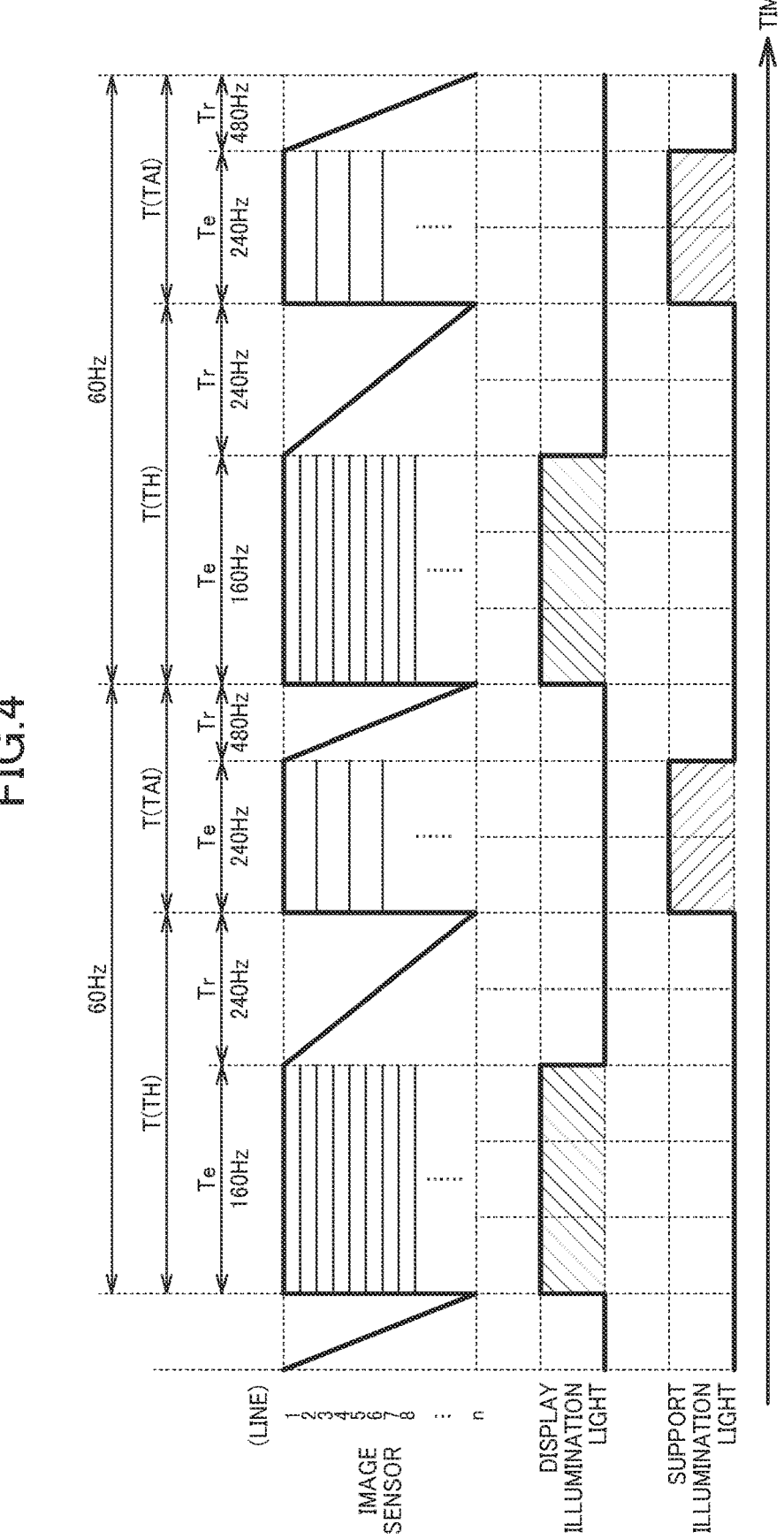
FIG. 4 is a chart showing a light emission sequence and an imaging sequence according to the second embodiment.

FIG. 3 is a diagram for explaining decimation readout according to the second embodiment. FIG. 4 is a diagram showing a light emission sequence and an imaging sequence according to the second embodiment.

As shown in FIG. 3, in the readout period Tr in the period TAI, the image sensor 114 selects alternate horizontal scanning lines from the first to n-th horizontal scanning lines, and reads out electric signals from pixels on the selected horizontal scanning lines. The alternate horizontal scanning lines are odd horizontal scanning lines or even horizontal scanning lines. FIGS. 3 and 4 each show an example in which the odd horizontal scanning lines are selected.

In FIG. 4, transverse lines indicated in the exposure period Te represent horizontal scanning lines from which signals are read out in the readout period Tr. In the readout period Tr in the period TH, the image sensor 114 sequentially selects the first to n-th horizontal scanning lines one by one, and reads out electric signals from all of the first to n-th horizontal scanning lines. In the readout period Tr in the period TAI, the image sensor 114 sequentially selects odd horizontal scanning lines from the first to n-th horizontal scanning lines, and reads out electric signals from n/2 horizontal scanning lines.

While the description has been given of the example in which readout target lines are decimated by readout of alternate lines, a decimation method is not limited thereto and the readout target lines may be decimated by, for example, binning. The binning mentioned herein is a method of reading out accumulated electric charges of a plurality of adjacent pixels to handle the plurality of pixels as a virtual one pixel. For example, in a case of 2×2 binning, the quantity of readout lines is reduced by half.

Figure 5:
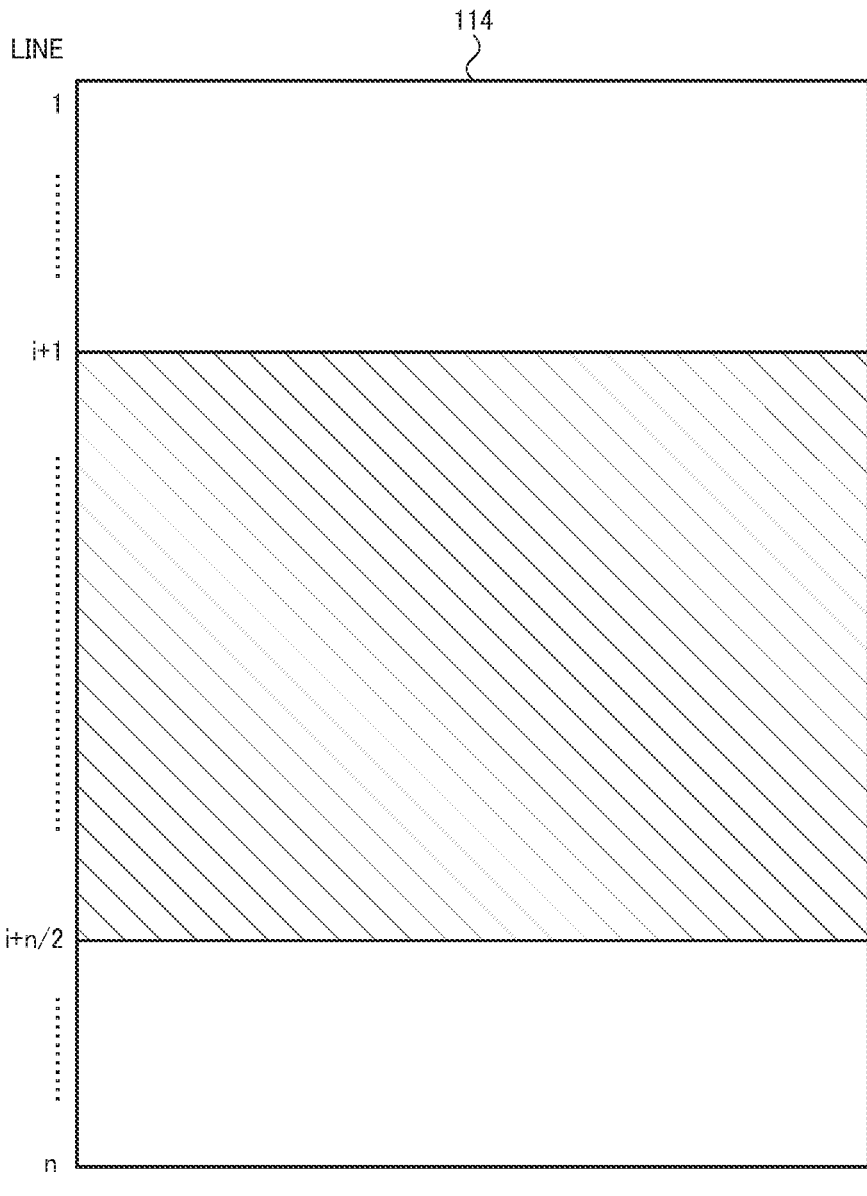
FIG. 5 is a diagram showing readout of a partial region according to a third embodiment.
Figure 6:
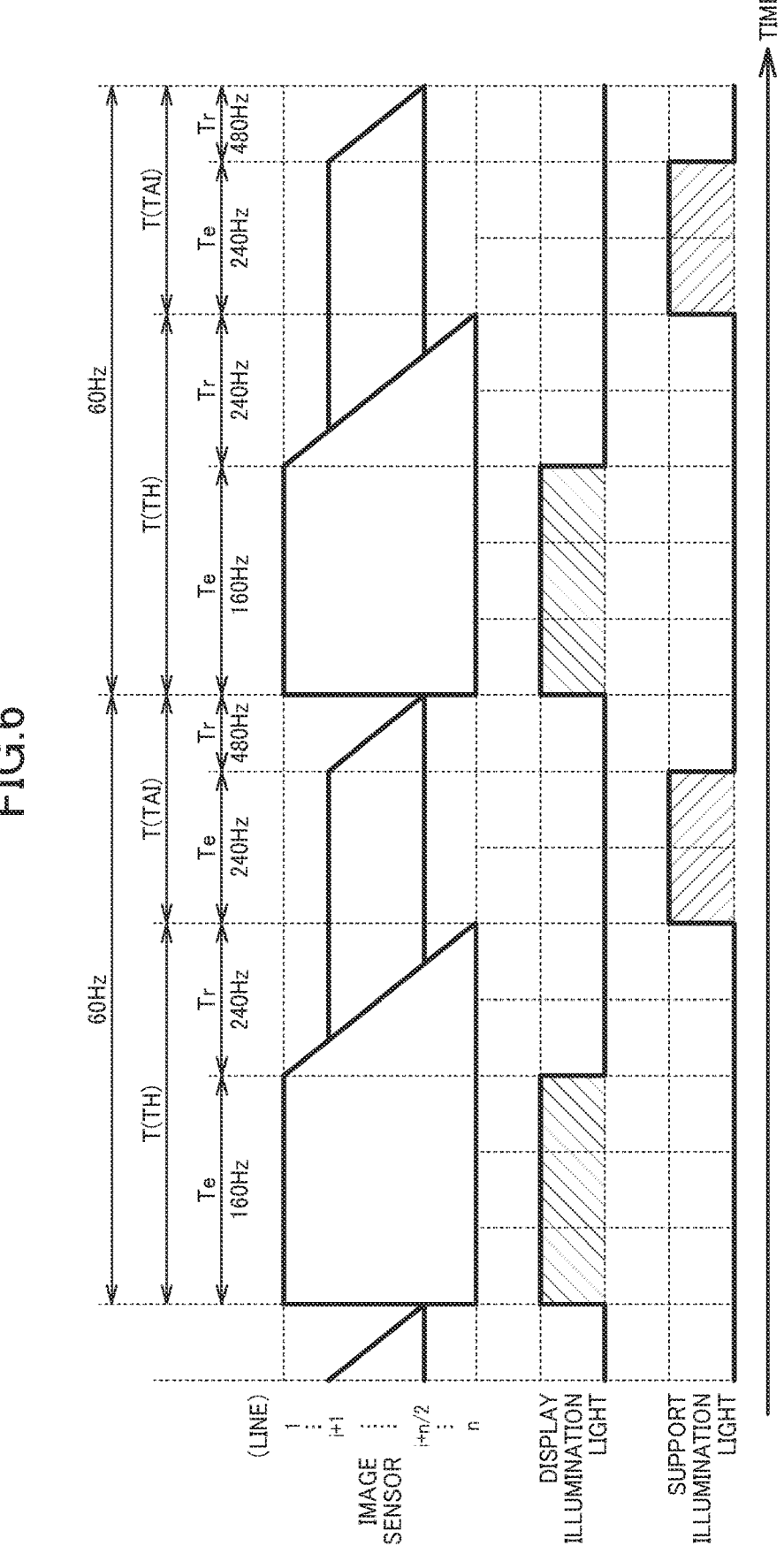
FIG. 6 is a chart showing a light emission sequence and an imaging sequence according to a third embodiment.

FIG. 5 is a diagram for explaining readout of a partial region according to the third embodiment. FIG. 6 is a diagram showing a light emission sequence and an imaging sequence according to the third embodiment.

As shown in FIG. 5, in the readout period Tr in the period TAI, the image sensor 114 selects consecutive n/2 horizontal scanning lines from the first to n-th horizontal scanning lines, and reads out electric signals from pixels on the selected horizontal scanning lines. Herein, n is an even number. The consecutive n/2 horizontal scanning lines are i+1-th to i+n/2-th horizontal scanning lines where i is an integer of 0 or more and n/2 or less.

Assume that a region in which pixels on the first to n-th horizontal scanning lines are arranged is defined as a first region, and a region in which the i+1-th to i+n/2-th horizontal scanning lines are arranged is defined as a second region. At this time, the imaging control section 211 is capable of freely setting a position of the second region in the first region.

For example, the imaging control section 211 sets the position of the second region based on input setting information. The setting information mentioned herein is information that designates the position of the second region, and is input by the user to the control device 200. In this case, the position of the second region is, for example, at the center of a screen, or slightly downward from the center of the screen.

Alternatively, the imaging control section 211 sets the position of the second region based on an image generated from first imaging signals or second imaging signals. The imaging control section 211 sets the second region at a relatively bright portion in the image. An index indicating brightness is, for example, a luminance value. Note that the region in which the second region is set is not limited to the bright region. For example, in a case where a region of interest such as a lesion is detected in the diagnosis support mode, the imaging control section 211 may set the second region so as to include the detected region of interest.

The above-mentioned control device 200 controls the image sensor 114 including a plurality of pixels. The control device 200 includes the imaging control section 211 that controls the image sensor 114. The imaging control section 211 performs control to read out, in a first readout period for readout of signals from a first quantity of pixels included in the plurality of pixels, the first imaging signals from the first quantity of pixels. The imaging control section 211 performs control to read out, in a second readout period for readout of signals from a second quantity of pixels that are included in the plurality of pixels and that are fewer than the first quantity of pixels, the second imaging signals from the second quantity of pixels. At this time, the second readout period is shorter than the first readout period. Note that in FIGS. 2, 4, and 6, the first readout period corresponds to the readout period Tr in the period TH, and the second readout period corresponds to the readout period Tr in the period TAI.

More specifically, the image sensor 114 is a rolling shutter-type image sensor. In the first readout period, the imaging control section 211 reads out the first imaging signals from pixels on a first quantity of horizontal scanning lines included in the plurality of horizontal scanning lines included in the image sensor 114. In the second readout period, the imaging control section 211 reads out the second imaging signals from pixels on a second quantity of horizontal scanning lines that are included in the plurality of horizontal scanning lines and that are fewer than the first quantity of horizontal scanning lines. Note that in FIGS. 2 to 6, the first quantity of lines correspond to the n lines, and the second quantity of lines correspond to the n/2 lines.

In the endoscope apparatus that comes with the diagnosis support function in the related art, an exposure period for capturing of an image to be used for display is shorter than a period for normal observation. Hence, there is an issue that a display image becomes dark. In this regard, according to the present embodiment, the quantity of pixels from which imaging signals are read out for generation of the support image is reduced in comparison to the quantity of pixels from which imaging signals are read out for generation of the normal image. With this configuration, the readout period Tr for readout of electric signals in the period TAI for capturing of the diagnosis support image can be set shorter. Assuming that a frame rate is constant, the exposure period Te in the period TH for capturing of the normal image can be set longer by the reduction of the readout period Tr in the period TAI, and thus a bright display image can be generated. In this manner, the quantity of readout pixels is optimized depending on the acquired image, whereby it is possible to provide the control device capable of acquiring the bright display image while acquiring the image used for extraction of the support information.

In the present embodiment, the second quantity of pixels may be pixels obtained by decimating some pixels of the first quantity of pixels.

More specifically, the first quantity of horizontal scanning lines are the first to n-th horizontal scanning lines as the plurality of horizontal scanning lines. The second quantity of horizontal scanning line are the odd horizontal scanning lines or the even horizontal scanning lines included in the first to n-th horizontal scanning lines.

According to the present embodiment, the pixels obtained by decimating some pixels of the first quantity of pixels are defined as the second quantity of pixels, whereby the second quantity of pixels become fewer than the first quantity of pixels, and the second readout period becomes shorter than the first readout period. With use of the decimation, a field of view of the image acquired from the second quantity of pixels becomes equivalent to a field of view of the image acquired from the first quantity of pixels, whereby the support information is generated based on the diagnosis support image in which the entire field of view is imaged. For example, the presence diagnosis mode, which will be described later, is used in screening of the lesion or the like. In this case, support information for detection of the lesion is preferably obtained from the entire field of view.

In the present embodiment, when a region in which the first quantity of pixels are located is defined as the first region of the image sensor 114 and a region in which the second quantity of pixels are located is defined as the second region of the image sensor 114, the second region may be a partial region of the first region.

More specifically, the first quantity of horizontal scanning lines are the first to n-th horizontal scanning lines as the plurality of horizontal scanning lines. The second quantity of horizontal scanning line are the i+1-th to i+n/2-th horizontal scanning lines included in the first to n-th horizontal scanning lines.

According to the present embodiment, part of the first region is defined as the second region, whereby the second quantity of pixels become fewer than the first quantity of pixels, and the second readout period becomes shorter than the first readout period. In addition, the part of the first region serves as the second region, whereby it is possible to obtain an identical resolution in the part of the second region both in the normal image and the diagnosis support image. Consequently, the support information is generated based on the diagnosis support image in which the resolution is not reduced in the second region. For example, the qualitative diagnosis mode, which will be described later, is used in detailed examination of the lesion or the like. In this case, support information for qualitative diagnosis is preferably obtained from a high-resolution image of the lesional portion.

In the present embodiment, the imaging control section 211 is capable of setting the position of the second region in a variable manner. For example, the imaging control section 211 sets the second region at the center of the image. Alternatively, the imaging control section 211 sets a relatively bright region in the image acquired from the first imaging signals or the second imaging signals as the second region.

According to the present embodiment, a freely selected region from which the support information is desired to be extracted can be set as the second region. A doctor who operates the endoscope 100 locates the lesion in the vicinity of the center of the image, and observes the lesion. In this case, the second region is preferably set at the center of the image. Additionally, the second region is preferably set at a position designated by the doctor in a variable manner. Alternatively, in a case where the lesion is detected by AI image recognition, the second region including the detected lesion is set, whereby the lesion can be analyzed by AI in a more detailed manner.

The control device 200 according to the present embodiment includes the light source section 240. The light source section 240 emits first illumination light, as the illumination light emitted toward the object, in a first exposure period before the first readout period. The light source section 240 emits second illumination light, as the illumination light emitted toward the object, in a second exposure period before the second readout period. The imaging control section 211 performs control to set at least the first quantity of pixels at an exposure state in the first exposure period. The imaging control section 211 performs control to set at least the second quantity of pixels at an exposure state in the second exposure period. Note that in FIGS. 2, 4, and 6, the first exposure period corresponds to the exposure period Te in the period TH, and the second exposure period corresponds to the exposure period Te in the period TAI.

More specifically, the second illumination light is light that is different in spectrum from the first illumination light. The first exposure period is shorter than the second exposure period.

According to the present embodiment, the first imaging signals obtained by imaging of the object illuminated with the first illumination light can be read out in the first readout period, and the second imaging signals obtained by imaging of the object illuminated with the second illumination light can be read out in the second readout period that is shorter than the first readout period. This enables readout of imaging signals in a readout period having a length according to the illumination light, and also enables extension of the first exposure period by the reduction of the second readout period.

The control device 200 according to the present embodiment includes the image generation section 213 and the support information generation section 214. The image generation section 213 generates a display image to be displayed on the display section 300 based on the first imaging signals. The support information generation section 214 generates the support information to support diagnosis or treatment based on the second imaging signals. At this time, the first illumination light is light for acquisition of the display image. The second illumination light is light for acquisition of the support information. In FIGS. 2, 4, and 6, the first illumination light corresponds to the display illumination light, and the second illumination light corresponds to the support illumination light.

According to the present embodiment, the first imaging signals obtained by imaging of the object illuminated with the display illumination light are read out in the first readout period, and the second imaging signals obtained by imaging of the object illuminated with the support illumination light are read out in the second readout period that is shorter than the first readout period. This enables extension of the first exposure period in which the object is illuminated with the display illumination light by the reduction of the second readout period, and thereby enables obtaining of a bright display image. The extended exposure period increases luminance of the display image, or reduces noise in the display image.

The control device 200 according to the present embodiment includes the support information generation section 214. The support information generation section 214 generates first support information to support diagnosis or treatment based on the second imaging signals in a first determination mode. The support information generation section 214 performs switching from the first determination mode to a second determination mode based on the first support information. The support information generation section 214 generates second support information that is different in content of diagnosis or treatment from the first support information based on the second imaging signals in a second determination mode. In the first determination mode, the second quantity of pixels are pixels obtained by decimating some pixels of the first quantity of pixels. In the second determination mode, when a region in which the first quantity of pixels are located is defined as the first region of the image sensor 114 and a region in which the second quantity of pixels are located is defined as the second region of the image sensor 114, the second region is a partial region of the first region. The first determination mode and the second determination mode will be described later, but as one example, the first determination mode is the presence diagnosis mode to make diagnosis of the presence of a lesion candidate included in the object, and the first support information is information indicating the presence of the lesion candidate. The second determination mode is the qualitative diagnosis mode to make diagnosis of the state of the lesion candidate, and the second support information is information indicating the state of the lesion candidate.

According to the present embodiment, it is possible to switch between decimation readout and partial region readout depending on a determination mode. For example, the presence diagnosis mode is used as the first determination mode in screening of the lesion or the like. In this case, the support information for detection of the lesion is preferably obtained from the entire field of view. In addition, the qualitative diagnosis mode is used as the second determination mode in detailed examination of the lesion or the like. In this case, the support information for qualitative diagnosis is preferably obtained from the high-resolution image of the lesional portion.

3. Second Configuration Example of Endoscope Apparatus

Figure 7:
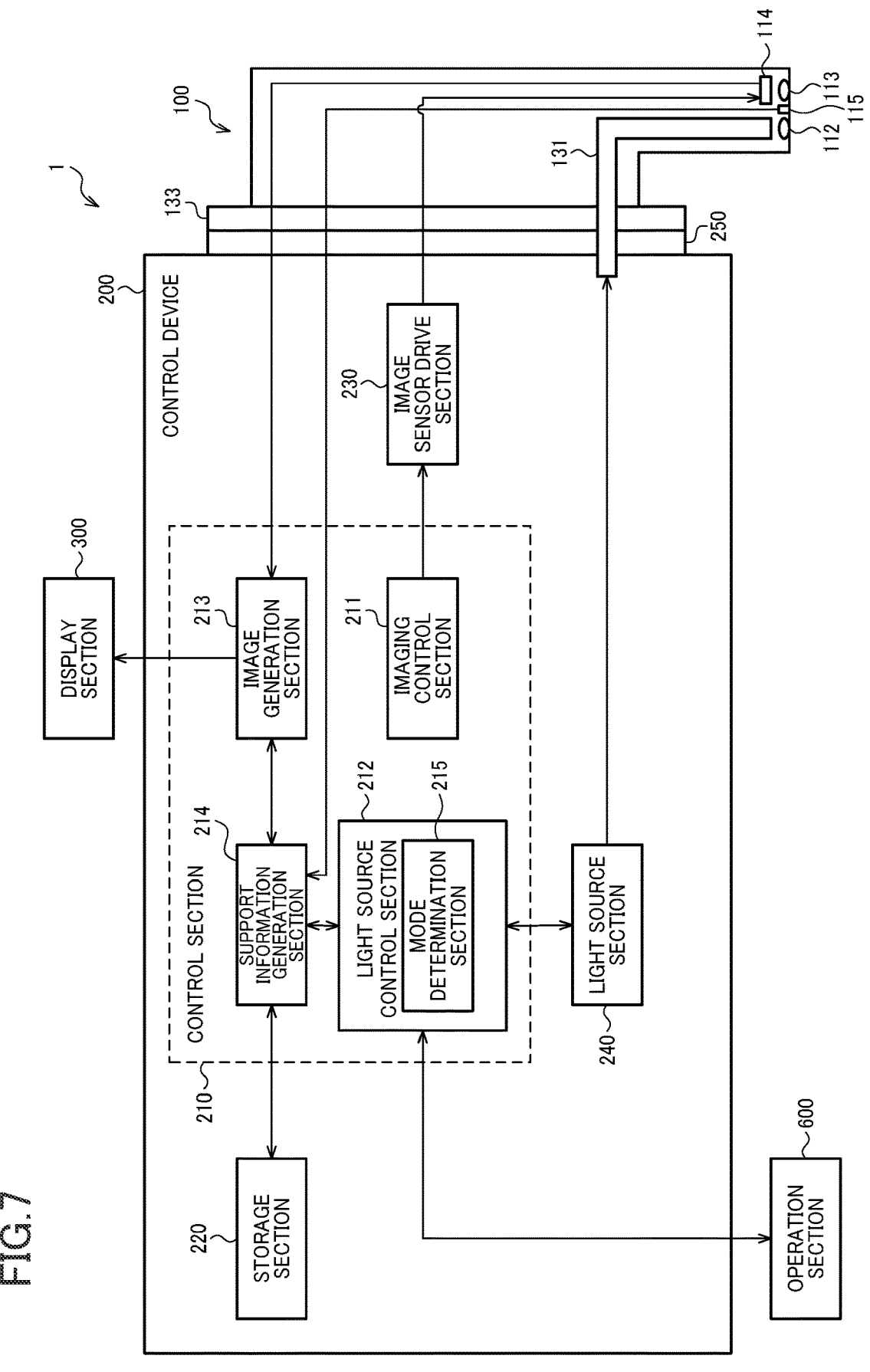
FIG. 7 shows a second configuration example of the endoscope apparatus.
Figure 8:
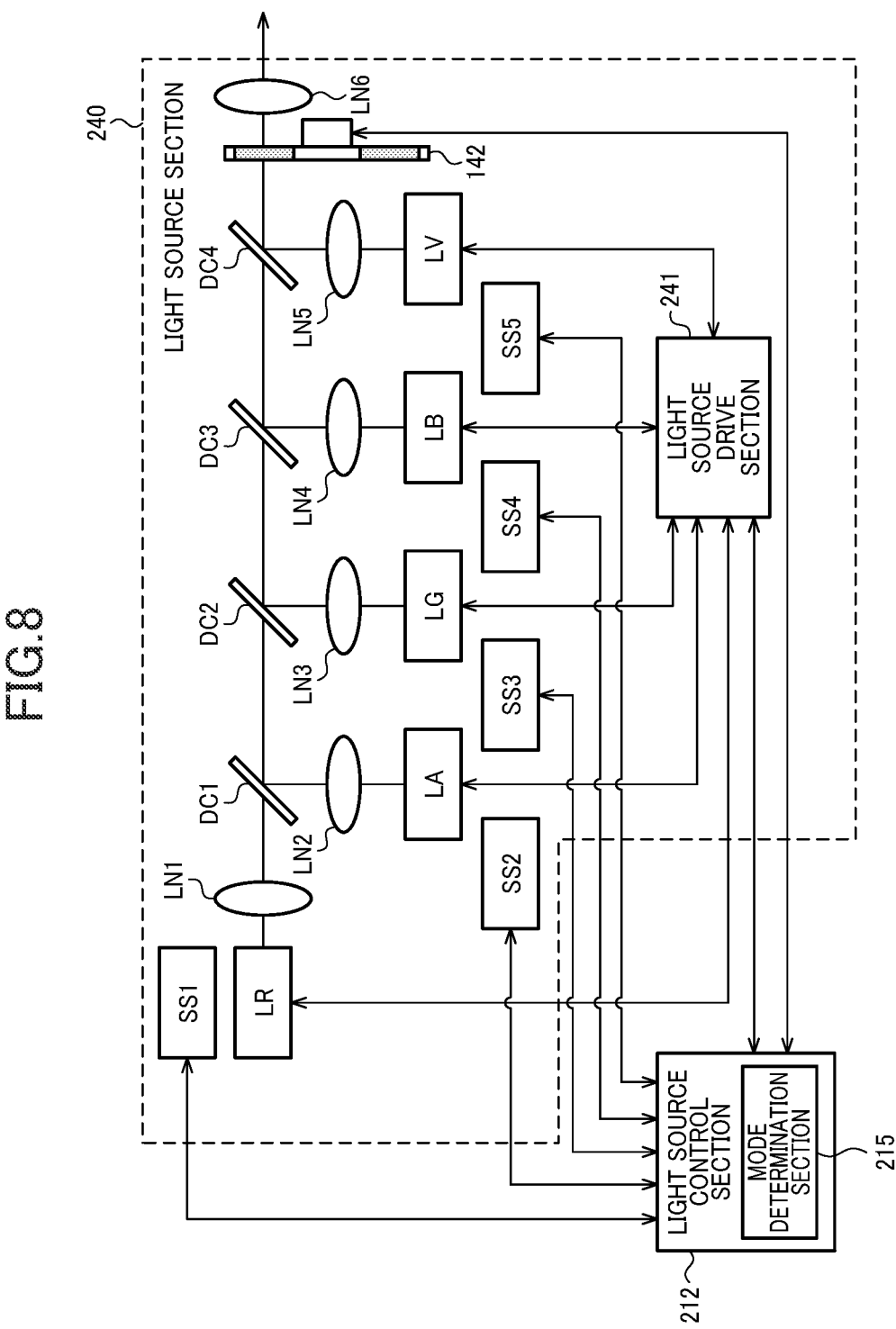
FIG. 8 shows a detailed configuration example of a light source section in the second configuration example.

FIG. 7 shows a second configuration example of the endoscope apparatus 1. FIG. 8 shows a detailed configuration example of the light source section 240 in the second configuration example. As shown in FIGS. 7 and 8, the endoscope apparatus 1 includes an operation section 600 in the second configuration example. In addition, the endoscope 100 includes a distance-measurement sensor 115. The light source control section 212 includes a mode determination section 215. In addition, the light source section 240 includes optical sensors SS1 to SS5. Note that a component that has been already described in the first configuration example is denoted by an identical reference sign, and a description thereof is omitted as appropriate.

The operation section 600 is a device for a user such as a doctor to operate the endoscope apparatus 1. The operation section 600 is, for example, a button, a dial, a foot switch, a touch panel, or the like.

The distance-measurement sensor 115 measures a distance from the leading end of the insertion section 110 to the object. The distance-measurement sensor 115 is a time-of-flight (TOF) distance-measurement sensor, an ultrasonic distance-measurement sensor, or the like. Instead of using the distance-measurement sensor, the objective optical system 113 may be substituted by a stereoscopic optical system to measure a distance. When the TOF distance-measurement sensor is used, there is a case where light with a long wavelength such as infrared light is used. Note that in an embodiment in which a distance-measurement function is not used, the distance-measurement sensor 115 may be omitted.

The optical sensors SS1, SS2, SS3, SS4, and SS5 are arranged at positions at which leaked light from the light sources LR, LA, LG, LB, and LV, respectively, can be detected. The leaked light mentioned herein is light emitted toward a portion that is not an optical path through which light is incident on the lenses LN1 to LN5. The light source control section 212 performs feedback control so that a light emission quantity of the light source LR becomes a desired value based on an output signal from the optical sensor SS1. Similarly, the light source control section 212 performs feedback control so that light emission quantities of the light sources LA, LG, LB, and LV become desired values based on respective output signals from the optical sensors SS2, SS3, SS4, and SS5, respectively.

The endoscope apparatus 1 has the presence diagnosis mode, the qualitative diagnosis mode, and a treatment support mode. Spectral characteristics of the support illumination light are different among the presence diagnosis mode, the qualitative diagnosis mode, and the treatment support mode. That is, the light source control section 212 controls the light source section 240 to generate support illumination light having spectral characteristics corresponding to a set mode. The light source control section 212 includes the mode determination section 215, which performs switching of the determination mode based on the support information generated by the support information generation section 214. Note that the switching of the determination mode may be performed based on information input via the operation section 600.

The determination mode is a mode corresponding to a determination criterion used when the support information generation section 214 generates the support information. That is, the support information generation section 214 in the first determination mode generates the support information based on a first determination criterion, and the support information generation section 214 in the second determination mode that is different from the first determination mode generates the support information based on a second determination criterion that is different from the first determination criterion. A determination criterion in each determination mode is only required to correspond to an observation purpose of the determination mode. That is, the support information that is required to be presented is different depending on an observation purpose, but a determination criterion with which the support information according to the observation purpose can be extracted from image information is only required to be adopted. For example, the control section 210 may estimate a determination mode based on the image information to set the estimated determination mode. The determination mode is set, whereby the determination criterion used when the support information is generated is set. The following description is given of a case where the first determination mode is the presence diagnosis mode and the second determination mode is the qualitative diagnosis mode as an example. However, the presence diagnosis mode and the qualitative diagnosis mode are examples of the determination mode set according to an observation mode for a doctor at the time of observation with the endoscope, but another predetermined determination mode may be adopted. A trained model corresponding to each determination mode is used in the following description, but the process is not limited thereto and is only required to be a process with a different criterion depending on a determination mode.

The support information is generated by the trained model corresponding to each determination mode. That is, the storage section 220 stores therein information of a trained model corresponding to the presence diagnosis mode, information of a trained model corresponding to the qualitative diagnosis mode, and information of a trained model corresponding to the treatment support mode. The support information generation section 214 performs an inference process based on the trained model corresponding to the set determination mode to generate the support information from image signals. The trained model in each determination mode is, for example, trained as described below. The following description is given of the presence diagnosis mode as an example, but the respective trained models in the qualitative diagnosis mode and the treatment support mode are trained also by a similar method.

Training data is an image captured with the support illumination light in the presence diagnosis mode and annotation information that is added by an expert such as a doctor to the image. The annotation information is information that is desired to be displayed as the support information, and is, for example, information indicating a position or contour of the lesional portion, or the like in the presence diagnosis mode. A plurality of sets of images and annotation information is prepared, and these sets serve as the training data. Images included in the training data are input to an inference algorithm, which infers the support information from the image. Feedback is given to a parameter of the inference algorithm so as to approximate the support information and the annotation information. The training is performed by repetition of the above-mentioned feedback using the plurality of sets of images and annotation information.

Various kinds of environments in which a training process is performed can be assumed. For example, the control section 210 of the endoscope apparatus 1 may execute the training process, and write information of the trained model generated by the training process in the storage section 220. Alternatively, an information processing device such as a personal computer (PC) may execute the training process, and write information of the trained model generated by the training process in the storage section 220 of the endoscope apparatus 1.

Note that the "lesion" in the present specification refers to a part detected as having a possibility for the lesion by the support information generation section 214, and whether or not the part is actually the lesion is determined by the doctor. That is, the "lesion" detected by the support information generation section 214 is the lesion candidate. In the present specification, the lesion candidate is also referred to simply as the lesion or the lesional portion.

4. Fourth Embodiment

A method of optimizing the illumination light according to the observation purpose is described below. In a fourth embodiment, switching from the presence diagnosis mode to the qualitative diagnosis mode is automatically performed based on the support information. As described above, each of the display illumination light and the support illumination light is emitted in a time-division manner, and the support illumination light is set to have optimal spectral characteristics in each of the presence diagnosis mode and the qualitative diagnosis mode.

First, a light emission sequence and an imaging sequence in each mode are described. In addition, contents of the support information and a method of displaying the support information will be described.

Figure 9:
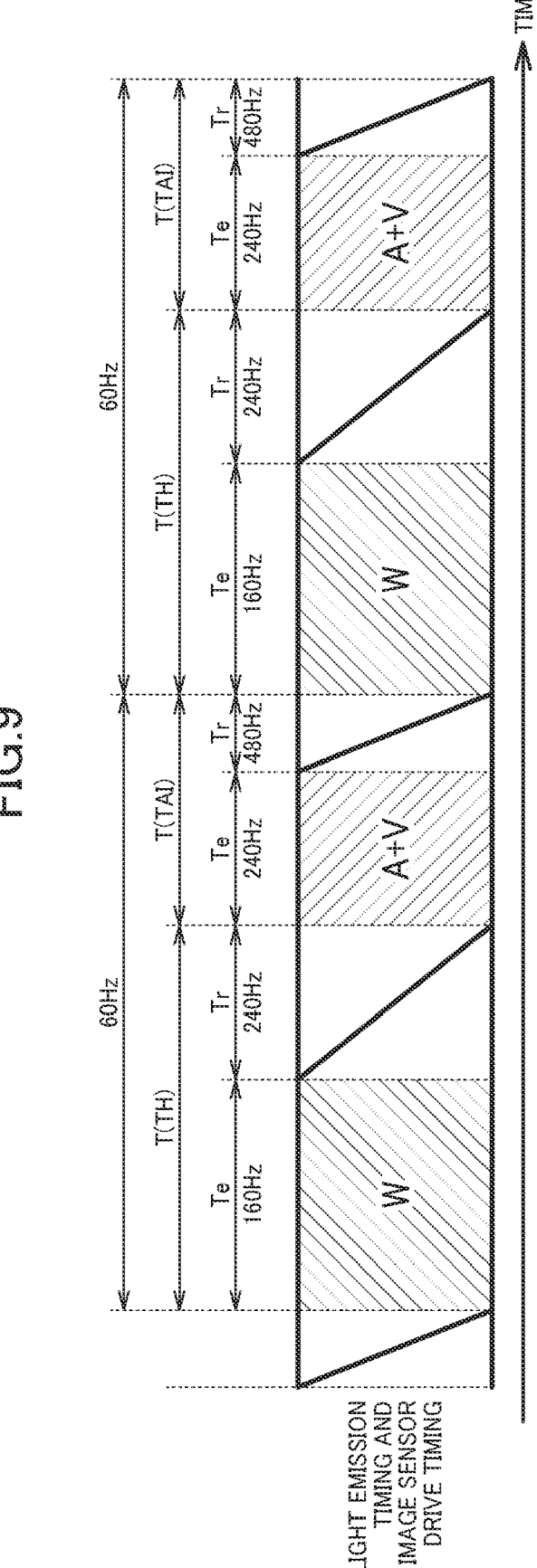
FIG. 9 is a chart showing a light emission sequence and an imaging sequence in a presence diagnosis mode.

FIG. 9 is a diagram showing a light emission sequence and an imaging sequence in the presence diagnosis mode. The light source control section 212 emits white light W as the display illumination light from the light source section 240 in the exposure period Te in the period TH. In the exposure period Te in the period TAI, the light source control section 212 causes the light source section 240 to emit the amber light A and the purple light V therefrom as the support illumination light. In a case where a frame rate is 60 Hz, a combined frame rate of the period TH and the period TAI is 60 Hz. As described above with reference to FIG. 2 or the like, the readout period Tr in the period TAI is shorter than the readout period Tr in the period TH. The exposure period Te in the period TH is longer than the exposure period Te in the period TAI.

The purple light is light appropriate for acquisition of features of superficial blood vessels in the mucosa or features of a structure of the duct of the gland. The amber light is light appropriate for acquisition of features such as deep blood vessels in the mucosa, redness, and inflammation. That is, the support information generation section 214 detects, as the support information, the lesion that is detectable based on the features of the superficial blood vessels in the mucosa or the features of the structure of the duct of the gland, or the lesion that is detectable based on the features of the deep blood vessels in the mucosa, redness, inflammation, or the like. In the presence diagnosis mode, with use of the purple light and the amber light, it becomes possible to detect the presence of a wide range of lesions such as cancer and an inflammatory disease.

Figure 10:
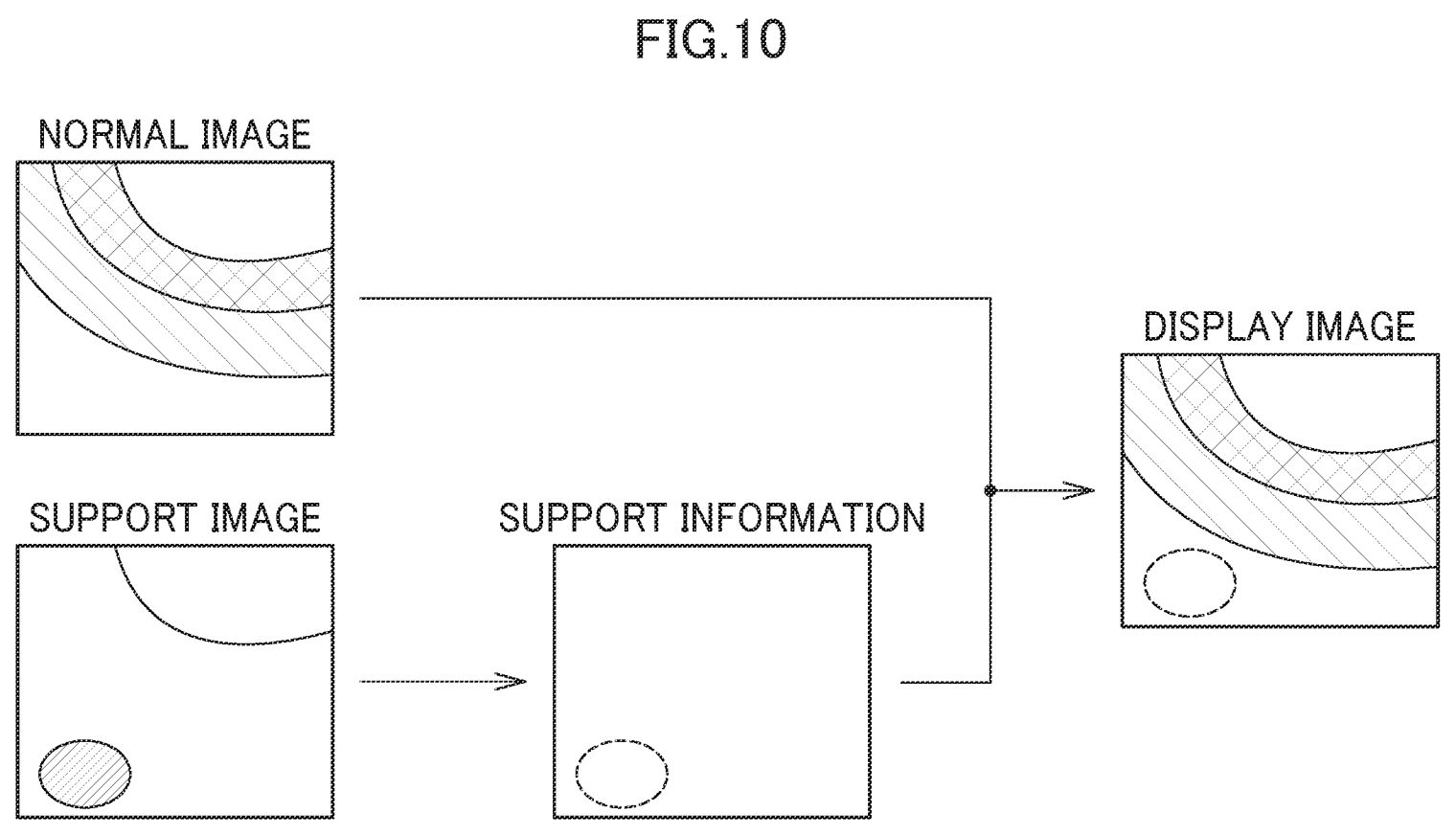

FIG. 10 is a diagram for explaining a generation process of generating the display image. The image generation section 213 generates the normal image from the image signals obtained by imaging performed in the period TH in FIG. 9. The normal image is the white light image.

Additionally, the image generation section 213 generates the support image from the image signals obtained by imaging performed in the period TAI in FIG. 9. The support image is a captured image of the object illuminated with the amber light and the purple light. The support information generation section 214 generates the support information from the support image. In FIG. 10, a hatched portion shown in the lower left of the support image is the lesion, and a contour thereof is detected as the support information. In FIG. 10, the contour of the lesion is indicated by a dotted line. Instead of generation of the support image by the image generation section 213, the image signal obtained by imaging performed in the period TAI may be directly input to the support information generation section 214.

The image generation section 213 uses the normal image as the display image, and further superimposes a display of the contour of the lesion on the display image. The display image to which the support information is added is displayed on the display section 300. The doctor or the like who uses the endoscope apparatus 1 sees the display image, and can thereby recognize the position, the contour, or the like of the lesion candidate. The doctor or the like has learned how the lesion appears in the normal image through experience or training. Hence, the normal image serves as the display image and the support information is added to the display image, whereby the doctor easily observes and makes diagnosis of the lesion.

Subsequently, a light emission sequence or the like in the qualitative diagnosis mode is described. A plurality of diagnosis modes can be provided as the qualitative diagnosis mode. In the fourth embodiment, a narrow band imaging (NBI) mode and a pseudo-staining mode are provided.

Figure 11:
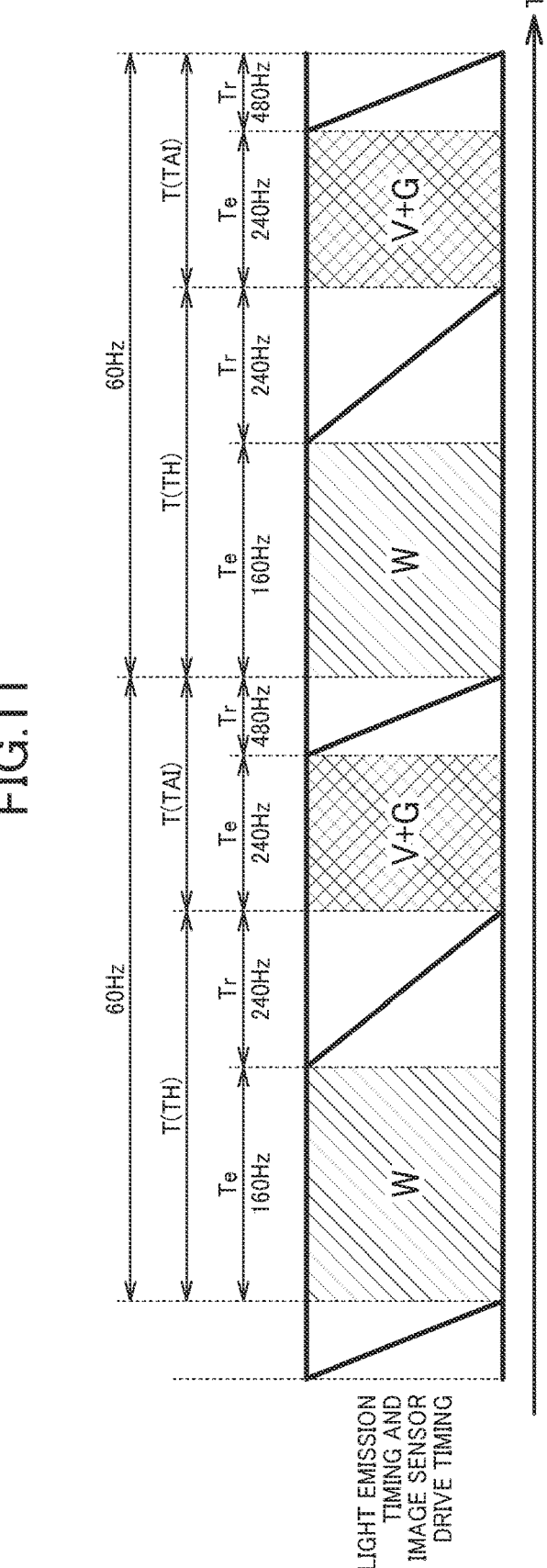
FIG. 11 is a chart showing a light emission sequence and an imaging sequence in a narrow band imaging (NBI) mode.

FIG. 11 is a diagram showing a light emission sequence and an imaging sequence in the NBI mode. A description about contents that are identical to those in FIG. 9 are omitted.

In the NBI mode, the light source control section 212 causes the light source section 240 to emit the purple light V and the green light G therefrom in the exposure period Te in the period TAI. A combination of the purple light V and the green light G is used in NBI. However, a light quantity ratio of the purple light V and the green light G is only required to be appropriate for the inference process with the AI, and is not necessarily a light quantity ratio in normal NBI.

The support information in the qualitative diagnosis mode such as the NBI mode is qualitative support information regarding the lesion detected in the presence diagnosis mode. As the qualitative support information, for example, various kinds of information that are used for diagnosis of the lesion such as a degree of lesion progression, a disease state, a range of the lesion, a boundary between the lesion and a normal part can be assumed. For example, the trained model is trained on classification according to a classification criterion designated by an academic conference or the like, and a result of the classification from the trained model may serve as the support information.

In the NBI mode, the support information generation section 214 performs a process based on the trained model corresponding to the NBI mode to generate more qualitative support information. The qualitative support information in the NBI mode is results of classification according to various kinds of NBI classification criteria. Examples of the NBI classification criteria include vessel plus surface (VS) classification, Japan NBI Expert Team (JNET) classification, NBI International Colorectal Endoscopic (NICE) classification, and endocytoscopy (EC) classification. The VS classification is a lesion classification criterion for the stomach. Each of the JNET classification, the NICE classification, and the EC classification is lesion classification criterion for the large intestine.

Figure 12:
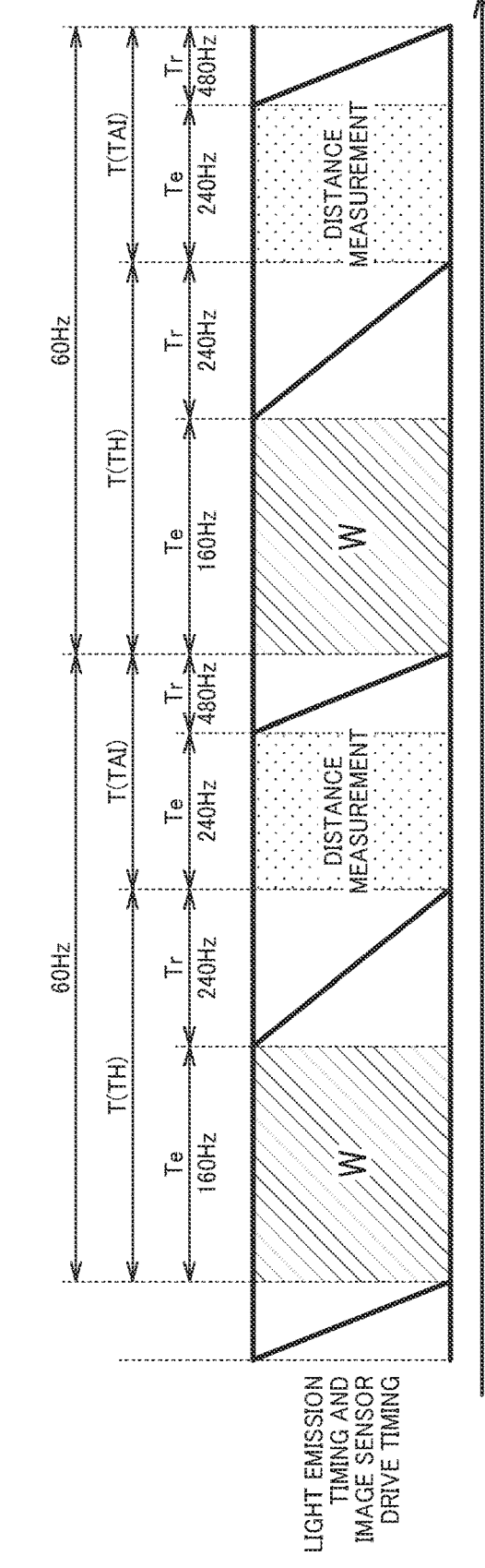
FIG. 12 is a chart showing a light emission sequence and an imaging sequence in a pseudo-staining mode.

FIG. 12 is a diagram showing a light emission sequence and an imaging sequence in the pseudo-staining mode. Note that a description about contents that are identical to those in FIG. 9 or the like are omitted.

In the pseudo-staining mode, the control section 210 uses the distance-measurement sensor 115 to measure a distance to the object in the exposure period Te in the period TAI. Specifically, the control section 210 acquires irregularities information of an object surface by the distance measurement. The irregularities information is, for example, a depth map or the like. The support information generation section 214 generates the support information based on a result of the distance measurement. The support information is information indicating pseudo-staining, and is, for example, information indicating light and dark in staining in each pixel. In staining by chemical spraying, a recess portion of the object surface is stained in a dark color. The support information generation section 214 generates the support information indicating such pseudo-staining as that reproduces staining by chemical spraying.

The image generation section 213 performs a staining process on the normal image captured with the display illumination light based on the support information to generate the display image. That is, the image generation section 213 adds a color to each pixel according to the light and dark of each pixel indicated by the support information. For example, in the pseudo-staining with indigocarmine, pseudo-staining is performed with blue that imitates indigo-carmine.

The support information generation section 214 generates qualitative support information from the display image subjected to the staining process based on the support information. The trained model corresponding to the pseudo-staining mode is trained on, as training data, the image subjected to the staining process and annotation information that is added to the image by the expert such as the doctor. The support information generation section 214 uses the trained model to generate the support information from a pseudo-stained image. In annotation, various kinds of classification criteria using staining by pigment spraying can be used. The support information generated by the support information generation section 214 is a result of classification according to a classification criterion used in training.

Figure 13:
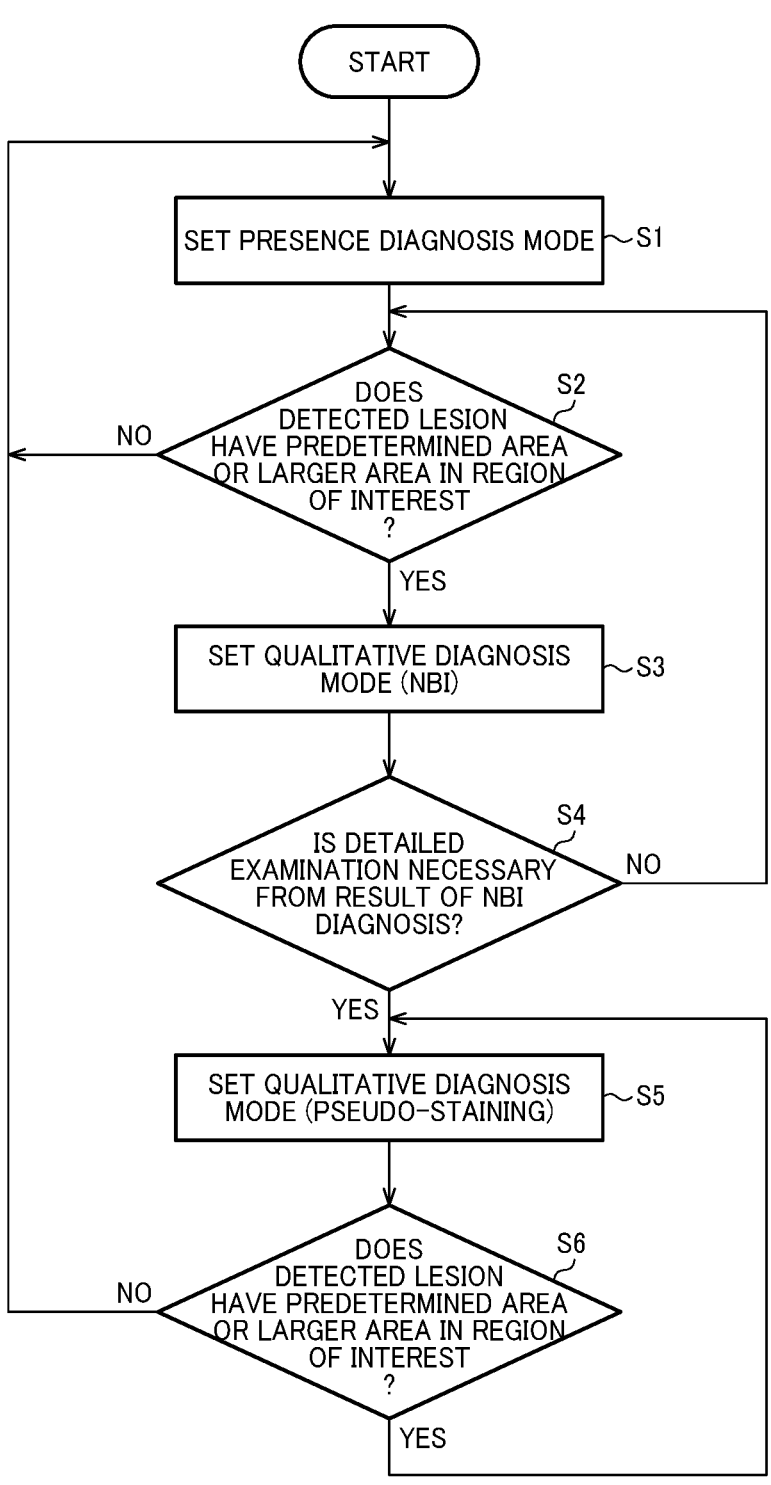
FIG. 13 is a flowchart describing procedures of a process performed by a processing section to switch from the presence diagnosis mode to a qualitative diagnosis mode.

Subsequently, a description is given of a method of automatically switching from the presence diagnosis mode to the qualitative diagnosis mode based on the support information. FIG. 13 is a flowchart describing procedures of a process performed by the control section 210 at the time of switching from the presence diagnosis mode to the qualitative diagnosis mode.

In step S1, the mode determination section 215 sets the presence diagnosis mode. The light source control section 212 causes the light source section 240 to emit the white light, the amber light A, and the purple light V therefrom in a time-division manner. The support information generation section 214 performs a process based on the trained model corresponding to the presence diagnosis mode to generate the support information.

Subsequently, in step S2, the mode determination section 215 determines whether or not the lesion indicated by the support information has a predetermined area or a larger area in a region of interest. In step S3, when the lesion has the predetermined area or larger area, the mode determination section 215 sets the NBI mode among the qualitative diagnosis modes. When the lesion has an area that is smaller than the predetermined area, the process returns to step S1.

Figure 14:
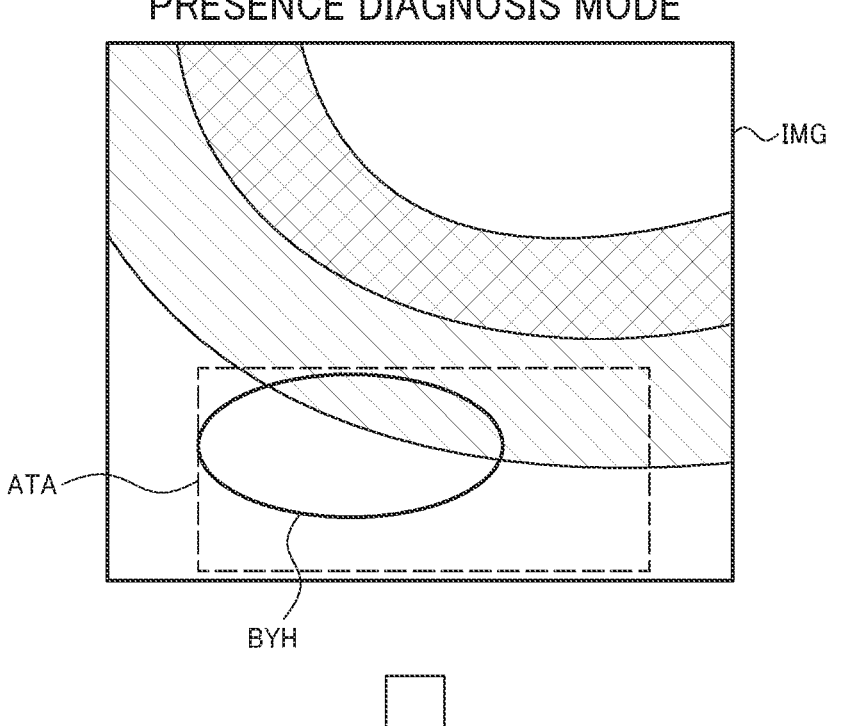
FIG. 14 is a diagram for explaining a method of determining whether or not to make a transition from the presence diagnosis mode to the qualitative diagnosis mode.

FIG. 14 is a diagram for explaining a method of determining whether or not to make a transition from the presence diagnosis mode to the qualitative diagnosis mode. An image IMG is an image captured in the presence diagnosis mode, and hatching in the image schematically indicates an object having a luminal form. The upper right of the image IMG indicates the back of a lumen, and a distance between a wall and an imaged portion becomes shorter toward the lower left. Assume that the support information generation section 214 detects a lesion BYH below the image IMG, that is, on the wall of the lumen. An ellipse indicated by a solid line is the support information generated by the support information generation section 214, and represents herein a contour of the lesion BYH.

A region of interest ATA is a region of interest. For example, the doctor who operates the endoscope apparatus 1 may use the operation section 600 to set the region of interest. The region of interest ATA can be set at a freely selected position and have a freely selected area in the image IMG. In FIG. 14, the region of interest ATA is set in a region below the image IMG. The mode determination section 215 calculates an area of the lesion BYH in the region of interest ATA, and determines whether or not the area is a predetermined value or more. For example, the mode determination section 215 counts a quantity of pixels in a portion in which the region of interest ATA and the lesion BYH overlap with each other. The mode determination section 215 determines whether or not the quantity of pixels is a predetermined value or more. Alternatively, the mode determination section 215 calculates a ratio of the counted quantity of pixels and the quantity of pixels of the region of interest ATA, and determines whether or not the ratio is a predetermined value or more. When determining that the area of the lesion BYH is the predetermined value or more, the mode determination section 215 makes a transition from the presence diagnosis mode to the NBI mode as the qualitative diagnosis mode. For example, the doctor who operates the endoscope apparatus 1 may use the operation section 600 to set a predetermined value for determination of the area.

In the NBI mode in step S3, the light source control section 212 causes the light source section 240 to emit the white light W, the purple light V, and the green light G therefrom in a time-division manner. The support information generation section 214 performs a process based on the trained model corresponding to the NBI mode to generate the support information. The support information generation section 214 generates qualitative support information regarding the lesion detected in the presence diagnosis mode.

Subsequently, in step S4, the mode determination section 215 determines whether or not further detailed examination is necessary based on the qualitative support information generated by the support information generation section 214. When it is determined that detailed examination is not necessary, the process returns to step S2. In step S5, when it is determined that detailed examination is necessary, the mode determination section 215 sets the pseudo-staining mode among the qualitative diagnosis modes.

In the pseudo-staining mode, each of illumination using the white light W and distance measurement is performed in a time-division manner. The support information generation section 214 performs a process based on the trained model corresponding to the pseudo-staining mode to generate the support information. The image generation section 213 performs a staining process on the display image based on the support information. The support information generation section 214 generates the qualitative support information from the display image subjected to the staining process based on the support information. That is, a result of the classification of the lesion according to the classification criterion using staining is generated as the support information.

Subsequently, in step S6, the mode determination section 215 determines whether or not the lesion detected in step S5 has a predetermined area or a larger area in the region of interest. A determination method is identical to that described in step S2. When the lesion has the predetermined area or a larger area, the process returns to step S5. When the lesion has an area that is smaller than the predetermined area, the process returns to step S1.

Figure 15:
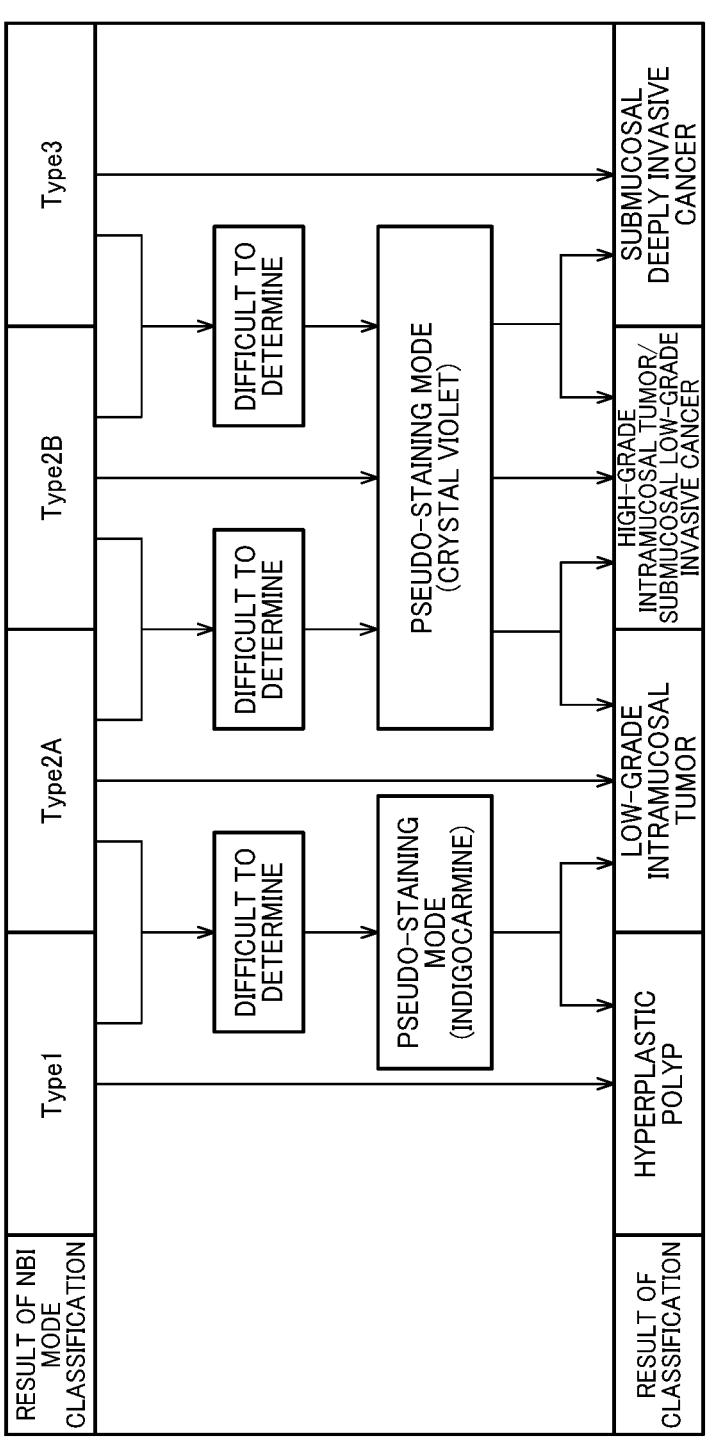
FIG. 15 shows an example of automatic classification in the qualitative diagnosis mode.

FIG. 15 shows an example of automatic classification in the qualitative diagnosis mode. FIG. 15 shows the flow of automatic classification using the JNET classification criterion. This flow is executed in steps S3 to S5 in FIG. 13.

In a training phase, the doctor tags the image with a result of the classification based on the JNET. That is, the doctor or the like uses a pointing device or the like to surround the lesional portion included in the image or performs other operations, and thereby tags the position or contour of the lesion with the classification of the lesion. The trained model is generated using the tag information and the image as the training data. When diagnosis using the endoscope apparatus is performed, the inference process using the above-mentioned trained model is performed, whereby the following automatic classification is implemented. That is, with the inference process, the position or contour of the lesion and the classification of the lesion are generated as the support information.

As shown in FIG. 15, in the NBI mode, the support information generation section 214 classifies the lesion detected in the presence diagnosis mode into Type 1, Type 2A, Type 2B, and Type 3. These types represent classifications characterized by a blood vessel pattern in the mucosa and the surface structure of the mucosa. The support information generation section 214 outputs a probability of the lesion being Type 1, a probability of the lesion being Type 2A, a probability of the lesion being Type 2B, and a probability of the lesion being Type 3. Note that not only a final result of the classification, but also a result of the classification in this phase may be displayed on the display image using characters or the like.

The support information generation section 214 determines whether or not the determination of the lesion is difficult based on the result of the classification in the NBI mode.

That is, when the probabilities of the lesion being Type 1 and Type 2A are equivalent, the support information generation section 214 determines that the determination is difficult. In this case, the mode determination section 215 sets the pseudo-staining mode to reproduce staining with indigocarmine in a pseudo manner. In this pseudo-staining mode, the support information generation section 214 classifies the lesion into a hyperplastic polyp or a low-grade intramucosal tumor based on the pseudo-stained image. These classifications are each characterized by a pit pattern in the indigocarmine stained image. In contrast, when the probability of the lesion being Type 1 is the threshold or more, the support information generation section 214 classifies the lesion into the hyperplastic polyp, and the mode determination section 215 does not make the transition to the pseudo-staining mode. When the probability of the lesion being Type 2A is the threshold or more, the support information generation section 214 classifies the lesion into the hyperplastic polyp, and the mode determination section 215 does not make the transition to the pseudo-staining mode.

When the probabilities of the lesion being Type 2A and Type 2B are equivalent, the support information generation section 214 determines that the determination is difficult. In this case, the mode determination section 215 sets the pseudo-staining mode to reproduce staining with crystal violet in a pseudo manner. In this pseudo-staining mode, the support information generation section 214 classifies the lesion into the low-grade intramucosal tumor, a high-grade intramucosal tumor, or submucosal low-grade invasive cancer based on the pseudo-stained image. These classifications are each characterized by a pit pattern in the crystal violet stained image.

Although details are omitted below, when the lesion is determined as Type 2B, the pseudo-staining mode to reproduce crystal violet staining in a pseudo manner is set, and the lesion is classified into the high-grade intramucosal tumor or the submucosal low-grade invasive cancer. When it is difficult to determine whether the lesion is Type 2B or Type 3, the pseudo-staining mode to reproduce crystal violet staining in a pseudo manner is set, and the lesion is classified into the high-grade intramucosal tumor, the submucosal low-grade invasive cancer, or submucosal deeply invasive cancer. When the lesion is determined as Type 2B, the lesion is classified into the submucosal deeply invasive cancer, and the mode determination section 215 does not make setting to make the transition to the pseudo-staining mode.

The image generation section 213 adds the above-mentioned result of the classification and the position or contour of the detected lesion, as the support information, to the display image, and causes the display section 300 to display the display image.

Figure 16:
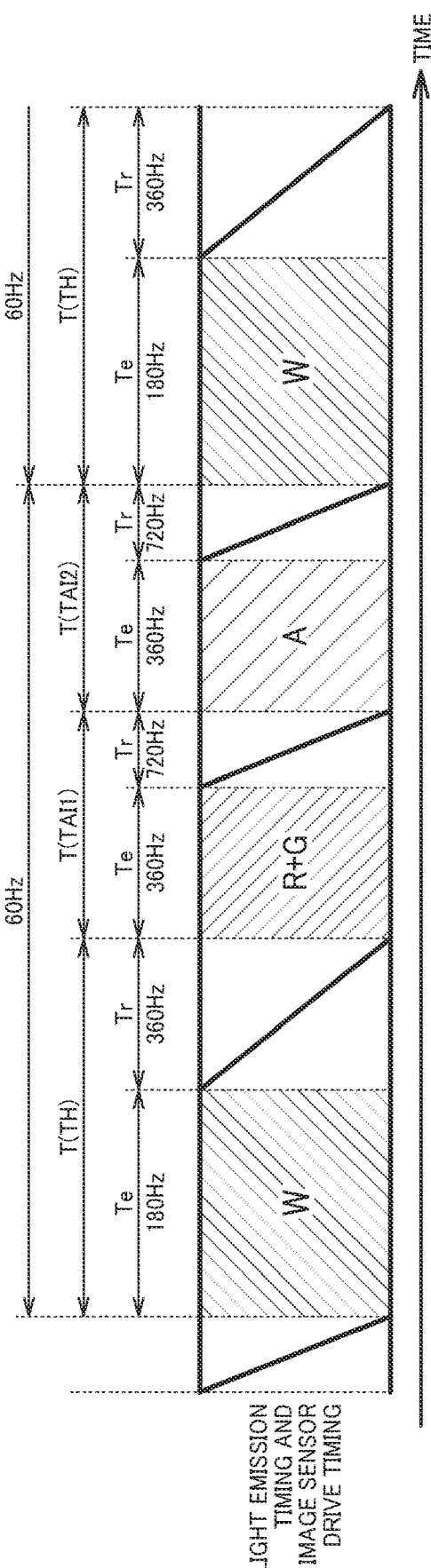
FIG. 16 is a chart showing a light emission sequence and an imaging sequence in an ulcerative colitis (UC) inflammation diagnosis mode.

While spectral characteristics of the support illumination light are changed according to a mode in the fourth embodiment, the process is not limited thereto, and a light quantity of the support illumination light, light distribution characteristics of the support illumination light, and an emission timing of the support illumination light may be changed according to the mode. For example, the light quantity may be set in the diagnosis support mode so that the lesional portion detected in the presence diagnosis mode is detected in appropriate brightness. Alternatively, the light distribution characteristics may be set in the diagnosis support mode so that the lesion detected in the presence diagnosis mode is illuminated appropriately. For example, a plurality of illumination lenses is arranged at the leading end of the endoscope 100 and a quantity of light emitted from each illumination lens is controlled, whereby distribution of light can be changed. An example of changing the emission timing will be described later with reference to, for example, FIG. 16 in a fifth embodiment. In FIG. 16, the support illumination light is emitted at two timings of the periods TAI 1 and TAI 2.

The endoscope apparatus 1 according to the above-mentioned embodiments includes the light source section 240, the image sensor 114, and the control section 210. The light source section 240 is capable of changing illumination characteristics including at least one of spectral characteristics of illumination light to be emitted, and a light quantity of the illumination light to be emitted, light distribution characteristics of the illumination light to be emitted, or an emission timing of the illumination light to be emitted. The image sensor 114 captures an image of the object illuminated with the illumination light, and outputs image signals. The control section 210 sets illumination characteristics based on the support information to support diagnosis or treatment. When the illumination characteristics are first illumination characteristics, the control section 210 changes the illumination characteristics to second illumination characteristics based on first support information generated based on the image signals.

Consequently, the illumination light can be optimized to have optimal illumination characteristics for the inference process with the AI, whereby it becomes possible to estimate the support information with high accuracy and present the highly accurate support information to the doctor or the like. Specifically, assumed is a case where AI that outputs the support information necessary for the observation purpose is used. At this time, the optimal illumination light for the inference process with the AI can be emitted from the light source section 240. This enables estimation of the support information according to the observation purpose with high accuracy.

Note that in the fourth embodiment, the first illumination characteristics correspond to the amber light A and the purple light V in the presence diagnosis mode; the second illumination characteristics correspond to the purple light V and the green light G in the NBI mode; the first support information indicates the position or contour of the lesion detected in the presence diagnosis mode; and the second support information indicates the result of classification of the lesion in the NBI mode.

In the present embodiment, the control section 210 generates the support information based on image signals. That is, the control section 210 generates the first support information based on the image signals when the illumination characteristics are the first illumination characteristics, and generates the second support information that is different in contents of diagnosis or treatment from the first support information based on the image signals when the illumination characteristics are the second illumination characteristics.

Figure 22:
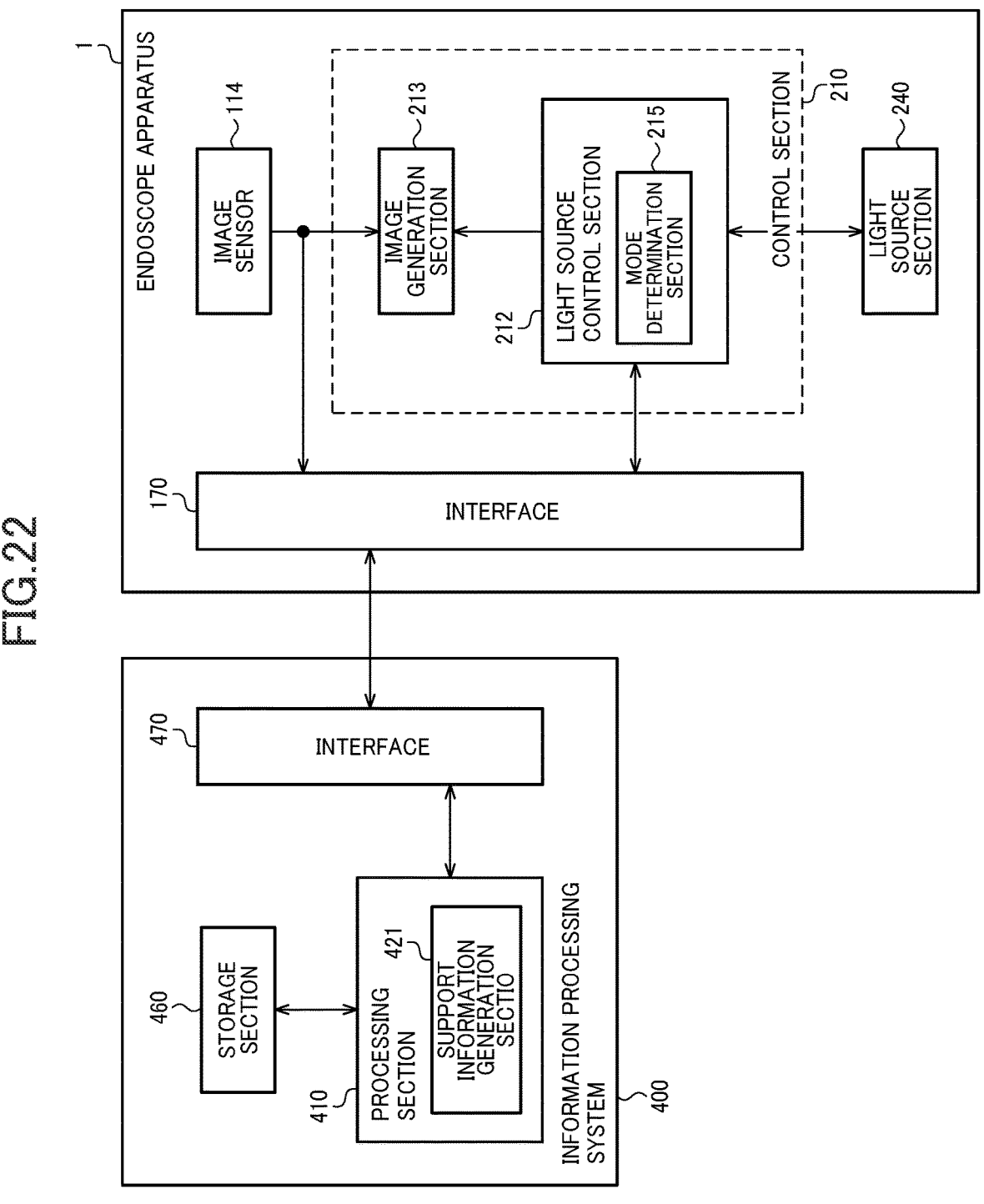
FIG. 22 shows a configuration example of an endoscope system.

As shown in FIG. 22, a support information generation section that generates the support information may be arranged outside the endoscope apparatus 1. An endoscope apparatus system shown in FIG. 22 includes the endoscope apparatus 1 and an information processing system 400. In FIG. 22, the control section 210 of the endoscope apparatus 1 does not include the support information generation section 214, and the endoscope apparatus 1 further includes an interface 170. The information processing system 400 includes an interface 470, a storage section 460, and a processing section 410. The processing section 410 includes a support information generation section 421.

The support information generation section 421 and the storage section 460 correspond to the support information generation section 214 and the storage section 220, respectively, shown in FIG. 1 or 7. That is, the image signals are input from the image sensor 114 to the support information generation section 421 via the interfaces 170 and 470. The support information generation section 421 performs the inference process based on the trained model stored in the storage section 460 to generate the support information from the image signals. The support information is input to the mode determination section 215 via the interfaces 470 and 170. The mode determination section 215 switches the determination mode based on the support information, and information of the determination mode is input to the support information generation section 421 via the interfaces 170 and 470.

As the interfaces 170 and 470, various kinds of communication interfaces can be assumed. For example, the interfaces 170 and 470 may be interfaces for network connection using a local area network (LAN), a wide area network (WAN), or the like. Alternatively, the interfaces 170 and 470 may be interfaces for wired communication with a universal serial bus (USB), or interfaces for wireless communication such as near field communication. The information processing system 400 may be, for example, an information processing device such as a PC and a server. Alternatively, the information processing system 400 may be a cloud system in which a plurality of information processing devices connected to a network performs an information process. In this case, functions of the processing section 410 are implemented by the information process performed by the plurality of information processing devices included in the cloud system.

In the present embodiment, when the determination mode in the generation process of generating the support information is the first determination mode, the control section 210 sets the first illumination characteristics and generates the first support information. The control section 210 switches the determination mode to the second determination mode based on the first support information. In the second determination mode, the control section 210 sets the second illumination characteristics and generates the second support information.

With this configuration, it is possible to automatically make a transition from the first determination mode to the second determination mode based on the first support information, and thereby emit illumination light having illumination characteristics corresponding to each determination mode. Consequently, it becomes possible to emit illumination light having optimal illumination characteristics in each determination mode, generate highly accurate or optimal support information in each determination mode, and present the support information to the doctor or the like.

In the present embodiment, the control section 210 determines whether or not the first support information satisfies a predetermined condition. When determining that the first support information satisfies the predetermined condition, the control section 210 switches the first determination mode to the second determination mode.

With this configuration, when the first support information satisfies the predetermined condition in the first determination mode, it is possible to automatically make a transition from the first determination mode to the second determination mode.

In the present embodiment, the first determination mode is the presence diagnosis mode to make diagnosis of the presence of a lesion candidate included in the object. The first support information is information indicating the presence of the lesion candidate. The second determination mode is the qualitative diagnosis mode to make diagnosis of the state of the lesion candidate. The second support information is information indicating the state of the lesion candidate.

With this configuration, it is possible to automatically make a transition from the presence diagnosis mode to the qualitative diagnosis mode based on the first support information in the presence diagnosis mode. The automatic transition from the presence diagnosis mode to the qualitative diagnosis mode enables automatic presentation of not only the presence of the lesion, but also qualitative information of the lesion to the doctor or the like. This enables automatic monitor display of the qualitative support information useful when the doctor or the like makes diagnosis of the lesion.

In the present embodiment, the control section 210 determines whether or not the first support information satisfies a predetermined condition that an area of the lesion candidate included in the first support information is a predetermined value or more or an observation magnification of the imaged portion is a predetermined value or more. When determining that the first support information satisfies the predetermined condition, the control section 210 switches the first determination mode to the second determination mode.

When the doctor pays attention to the lesion and brings the endoscope 100 closer to the lesion, the area of the lesion candidate can be assumed to be the predetermined value or more. Alternatively, extended observation is performed when the doctor tries to observe the lesion. For this reason, the transition to the diagnosis support mode is made when the area of the lesion candidate is the predetermined value or more or the observation magnification of the imaged portion is the predetermined value or more, whereby the qualitative support information regarding the lesion to which the doctor pays attention can be presented to the doctor.

In the present embodiment, the lesion candidate is a tumor candidate.

According to the present embodiment, the tumor candidate is detected in the presence diagnosis mode, and the transition to the qualitative diagnosis mode can be made when the tumor candidate satisfies the above-mentioned predetermined condition. This enables presentation of the qualitative support information of the tumor candidate, for example, a type of the tumor or the like, to the doctor. Note that the lesion is not limited to the tumor, and is only required to be an abnormal region in the living body. For example, the lesion may be inflammation, a bleeding region, or the like.

In the first determination mode, illumination light having the first illumination characteristics includes a first group of light that is at least one type of light among light in a plurality of colors. In the second determination mode, illumination light having the second illumination characteristics includes a second group of light that is at least one type of light among light in the plurality of colors and that is different from light of the first group.

With this configuration, it is possible to differentiate spectral characteristics of illumination light in the first determination mode and spectral characteristics of illumination light in the second determination mode. This enables generation of the support information using illumination light having optimal spectral characteristics in each determination mode. Note that a case where each group is made of light in a single color is included. The first group and the second group are only required to include partially different light and may include overlapping light. For example, in the examples shown in FIGS. 9 and 11, the first group corresponds to A and V, and the second group corresponds to V and G. In this examples, the first group and the second group have overlapping light of V, but are different in combination of colors.

In the present embodiment, the light in the plurality of colors includes the purple light, the amber light, and the green light.

With this configuration, it is possible to obtain information of superficial blood vessels in the mucosa with the purple light or the green light, and extract the support information from the information. However, the purple light allows for obtaining of information of shallow blood vessels in comparison with the green light. With the amber light, it is possible to obtain information of deep blood vessels in the mucosa or information of a hemoglobin concentration in a puddle of blood or the like, and extract the support information from these pieces of information.

In the present embodiment, the determination mode is the presence diagnosis mode to make diagnosis of the presence of the lesion candidate included in the object or the qualitative diagnosis mode to make diagnosis of the state of the lesion candidate. Alternatively, the determination mode may be the treatment support mode to support treatment. The treatment support mode will be describe later with reference to the subsequent embodiments.

Illumination light in the qualitative diagnosis mode includes light that is used for observation of inflammation, middle blood vessels, and deep blood vessels and that is not included in the illumination light in the presence diagnosis mode. This illumination light includes light having a wavelength longer than that of the illumination light in the presence diagnosis mode. Specifically, the illumination light in the presence diagnosis mode includes the purple light and the amber light. The illumination light in the qualitative diagnosis mode includes the purple light and the green light. Alternatively, as described later in the subsequent embodiments, the illumination light in the qualitative diagnosis mode may include the green light, the amber light, the red light, or illumination light for distance measurement.

Consequently, with use of the purple light or the green light, it is possible to capture a high contrast image of superficial blood vessels in the mucosa. In addition, with use of the amber light, it is possible to capture a high contrast image of deep blood vessels in the mucosa, the light and dark of blood in the bleeding region, or the like. With use of the purple light and the amber light in the presence diagnosis mode, it is possible to extract various types of lesion candidates. By combining the purple light and the green light in the qualitative diagnosis mode, it is possible to obtain the support information according to NBI diagnosis. By combining the green light, the amber light, and the red light in the qualitative diagnosis mode, it is possible to obtain, for example, the support information regarding an inflammatory disease such as ulcerative colitis from information of superficial blood vessels and deep blood vessels. With use of the illumination light for distance measurement in the qualitative diagnosis mode, it is possible to obtain, for example, the support information regarding the state of the mucosa or the lesion such as cancer from information of the shape or structure of the mucosa.

As described later in the subsequent embodiments, the illumination light in the treatment support mode may include light used for extraction of a lesion range or extraction of a bleeding point in a generation process of generating the support information. Specifically, the illumination light in the treatment support mode may include the purple light, the amber light, the illumination light for distance measurement, each of which is narrowband light. Alternatively, the illumination light in the treatment support mode may include the red light and the amber light that is the narrowband light.

By combining the purple light, the amber light, and the illumination light for distance measurement in the treatment support mode, it is possible to extract the lesion range as the support information from the information of the superficial blood vessels and the deep blood vessels and the information of the shape or structure of the mucosa. This enables presentation of the lesion range to the doctor or the like and enables support for, for example, treatment such as resection of the lesion. Additionally, by combining the red light and the amber light in the treatment support mode, it is possible to obtain information of the bleeding point in a puddle of blood or the like from light and dark information of hemoglobin.

In the present embodiment, the endoscope apparatus 1 includes the display section 300 that displays the display image. The light source section 240 emits, in a time division manner, the display illumination light to be used for generation of the display image and the support illumination light that is different in illumination characteristics from the display illumination light. The control section 210 generates the display image based on image signals obtained when the display illumination light is emitted. The control section 210 generates the support information based on image signals obtained when the support illumination light is emitted. The control section 210 then performs an image process to add a display content based on the support information to the display image.

The support illumination light is optimized for the inference process with the AI, and thus is not necessarily appropriate for observation. In the present embodiment, since the display image is captured with the display illumination light that is different from the support illumination light, it is possible to present the display image that is appropriate for observation to the doctor. Additionally, according to the present embodiment, based on the support information generated by the support information generation section 214, a display content corresponding to the support information is displayed on the display section 300. Since the illumination characteristics are optimized according to the observation purpose, it is possible to present the highly accurate support information generated from the image captured with the illumination light to the doctor, and support diagnosis or treatment.

In the present embodiment, the display content based on the support information is at least one of the position or contour of a target portion indicated by the support information.

This allows the display section 300 to display at least one of the position or contour of the target portion detected by the support information generation section 214. For example, in the presence diagnosis mode, the display section 300 is caused to display at least one of the position or the contour, whereby the presence of the lesion candidate can be presented to the doctor.

In the present embodiment, when the illumination characteristics of the support illumination light are the first illumination characteristics, the control section 210 performs an image process to generate the first support information and add a first display content to the display image based on the first support information. The control section 210 changes illumination characteristics of the support illumination light to second illumination characteristics based on the first support information, and generates the second support information. The control section 210 performs an image process to add a second display content that is different from the first display content to the display image based on the second support information.

This allows the highly accurate support information obtained with the illumination light having optimized illumination characteristics to be displayed on the display image captured with the display illumination light. In addition, the support information that is different in content depending on illumination characteristics can be obtained and can be displayed on the display image. This enables presentation of the display image that is appropriate for observation to the doctor so that various kinds of support information according to the observation purpose are superimposed on the display image.

In the present embodiment, the display illumination light is the white light. The support illumination light includes at least one of the purple light, the amber light, or the green light.

With this configuration, it is possible to display a white light image as the display image on the display section 300, and present the white light image to which the support information is added to the doctor. The support illumination light includes at least one of the purple light, the amber light, or the green light, whereby the illumination characteristics according to the observation purpose can be implemented. That is, with use of the purple light or the green light, it is possible to capture a high contrast image of superficial blood vessels in the mucosa. In addition, with use of the amber light, it is possible to capture a high contrast image of deep blood vessels in the mucosa, the light and dark of blood in the bleeding region, or the like. Alternatively, it is conceivable to combine these types of light according to the observation purpose. For example, in a case where the support information according to NBI diagnosis is desired to be obtained, it is only required to combine the purple light and the green light.

In the present embodiment, the endoscope apparatus 1 includes the storage section 220 that stores information of the trained model. The trained model is a model that has been trained to output the support information in response to the image signals. The control section 210 performs a process based on the trained model to generate the support information from the image signals.

With this configuration, execution of the inference process with the AI enables generation of the support information from the image signals. Training the trained model with training data created by the expert such as the doctor enables generation of the trained model that reflects expertise of the expert. With use of such a trained model, the support information based on the expertise of the expert can be presented to the user of the endoscope apparatus 1.

As described above, the trained model can include a neural network. As the neural network, various known AI technologies can be adopted. To utilize the neural network, it is necessary to develop software for training and execution of an inference algorithm, but a plurality of software packages that has been commercialized and open to the public for free is currently available and can be utilized. As an algorithm for machine learning in the neural network, various kinds of known training algorithms can be adopted and a supervised training algorithm using, for example, a backpropagation method can be adopted.

In the present embodiment, the storage section 220 stores information of a first trained model and a second trained model. The first trained model is a model that has been trained to output the first support information in response to the image signals obtained when the illumination characteristics are the first illumination characteristics. The second trained model is a model that has been trained to output the second support information in response to the image signals obtained when the illumination characteristics are the second illumination characteristics. When the illumination characteristics are the first illumination characteristics, the control section 210 performs a process based on the first trained model to generate the first support information. When the illumination characteristics are the second illumination characteristics, the control section 210 performs a process based on the second trained model to generate the second support information.

According to the present embodiment, the trained model corresponding to each illumination characteristics is prepared, whereby the support information can be generated by using the trained model according to the observation purpose. That is, not only the illumination characteristics, the AI is also optimized according to the observation purpose. This enables presentation of the highly accurate support information according to the observation purpose to the doctor.

5. Fifth Embodiment

In a fifth embodiment, the qualitative diagnosis mode is a UC inflammation diagnosis mode. The UC mentioned herein is ulcerative colitis. Since a method of making a transition from the presence diagnosis mode to the qualitative diagnosis mode is similar to that in the fourth embodiment, the following description is given of the UC inflammation diagnosis mode.

FIG. 16 is a diagram showing a light emission sequence and an imaging sequence in the UC inflammation diagnosis mode. Note that a description about contents that are identical to those in FIG. 9 or the like are omitted.

The light source control section 212 causes the light source section 240 to emit the white light therefrom in the exposure period Te in the period TH. In the UC inflammation diagnosis mode, the support illumination light is the red light R, the green light G, and the amber light A. The light source control section 212 causes the light source section 240 to emit the red light R and the green light G therefrom in the exposure period Te in a period TAI1, and causes light source section 240 to emit the amber light A therefrom in the exposure period Te in a period TAI2. In a case where a frame rate is, for example, 60 Hz, a combined frame rate of the period TH, the period TAI1, and the period TAI2 is 60 Hz. Each of the readout period Tr in the period TAI1 and the readout period Tr in the period TAI2 is shorter than the readout period Tr in the period TH. The exposure period Te in the period TH is longer than each of the exposure period Te in the period TAI1 and the exposure period Te in the period TAI2. Note that each of the red light R and the amber light A belongs to a red region, and for example, passes a red filter in a primary color Bayer-type imager. For this reason, each of the red light R and the amber light A is emitted in a time-division manner. The order of emission of the red light R and the amber light A may be reversed.

The combination of the red light R, the green light G, and the amber light A is illumination light appropriate for imaging of deep blood vessels in the mucosa. The qualitative support information in the UC inflammation diagnosis mode is a result of diagnosis or a result of classification based on viewability of the deep blood vessels. Note that the viewability does not mean that the deep blood vessels are actually seen by a human, but means, for example, contrast or the like of the deep blood vessels in the image. For example, the support information generation section 214 generates an inflammation level obtained by conversion of the contrast of the deep blood vessels into a numeric value as the support information.

Figure 17:
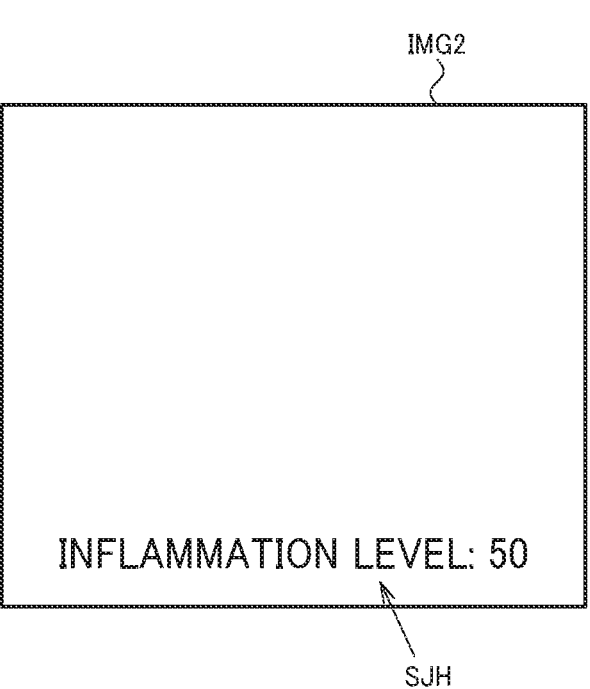
FIG. 17 shows an example of support information in the UC inflammation diagnosis mode.

FIG. 17 shows a display example of the support information in the UC inflammation diagnosis mode. The image generation section 213 superimposes inflammation level information SJH generated by the support information generation section 214 on a normal image IMG2 captured with the white light. For example, in a case where a numeric value of the inflammation level is 50, the image generation section 213 displays characters of "INFLAMMATION LEVEL: 50" in the lower portion of the normal image IMG2. The numeric value of the inflammation level changes according to a numeric value determined by the support information generation section 214. The doctor or the like can make diagnosis of the inflammation level of UC with reference to the displayed normal image and the displayed numeric value of the inflammation level.

6. Sixth Embodiment

In a sixth embodiment, the treatment support mode can be set. The treatment support mode according to the sixth embodiment is a range diagnosis mode to estimate a resection range of the lesion. For example, the range diagnosis mode is selected based on input from the operation section 600. Alternatively, a method similar to the method of automatically making the transition from the presence diagnosis mode to the qualitative diagnosis mode in the fourth embodiment may be used to make a transition from the presence diagnosis mode to the range diagnosis mode. Still alternatively, a transition from the qualitative diagnosis mode to the range diagnosis mode may be made. For example, when it is determined that the area of the lesion is the predetermined value or more in step S6 in FIG. 13, the transition to the range diagnosis mode may be made.

Figure 18:
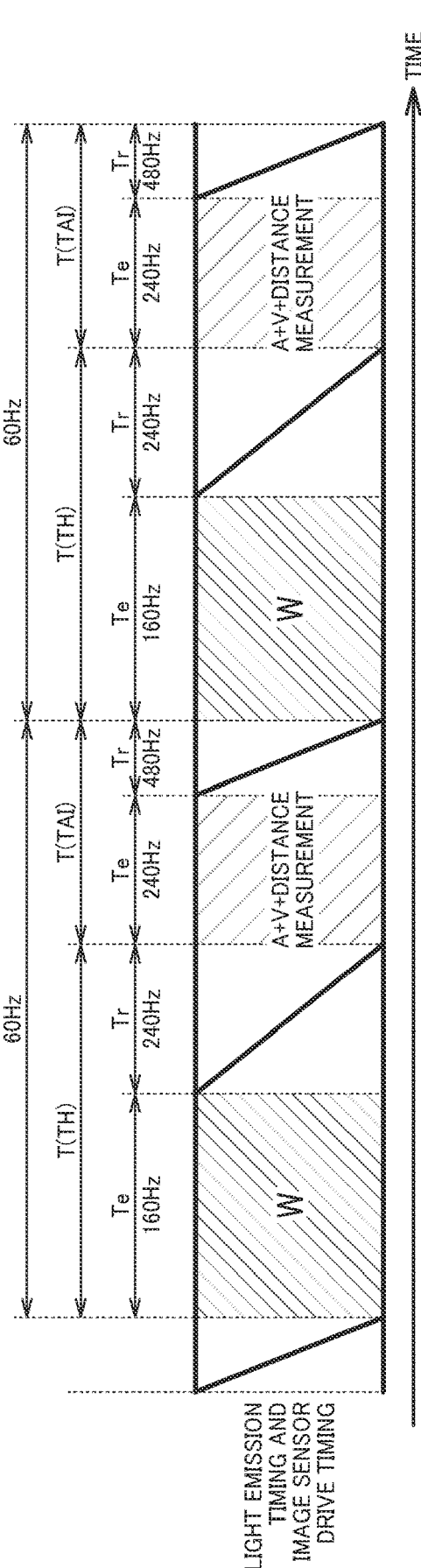
FIG. 18 is a chart showing a light emission sequence and an imaging sequence in a range diagnosis mode.

FIG. 18 is a diagram showing a light emission sequence and an imaging sequence in the range diagnosis mode. Note that a description about contents that are identical to those in FIG. 9 or the like are omitted.

In the exposure period Te in the period TAI, the light source control section 212 causes the light source section 240 to emit the amber light A and the purple light V therefrom. In the exposure period Te in the period TAI, the control section 210 uses the distance-measurement sensor 115 to measure a distance to the object. That is, the control section 210 generates a depth map or the like indicating irregularities information of the object surface.

Each of the amber light A and the purple light V as the support illumination light is identical to the support illumination light in the presence diagnosis mode. The support information generation section 214 uses a trained model similar to that used in the presence diagnosis mode to detect the position or contour of the lesion.

Figure 19:
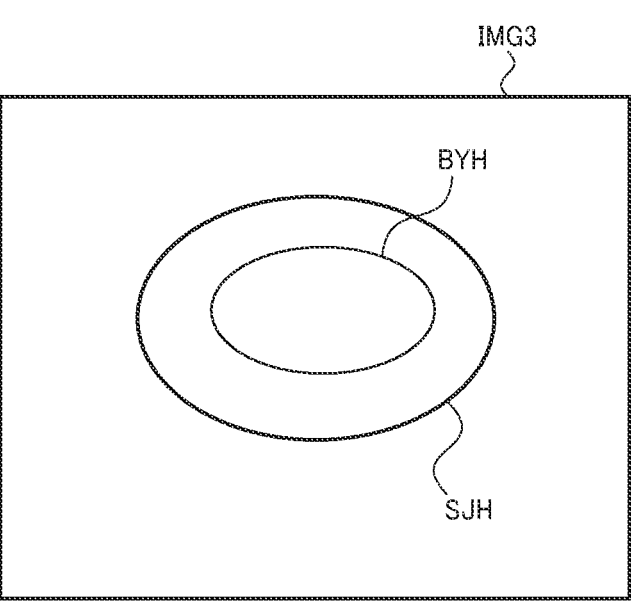
FIG. 19 shows an example of a display image in the range diagnosis mode.

FIG. 19 shows an example of a display image in the range diagnosis mode. The image generation section 213 displays the position or contour of the lesion BYH detected by the support information generation section 214 on a display image IMG3.

In addition, the support information generation section 214 estimates a resection range SJH of the lesion based on the object surface irregularities information obtained by distance measurement and the above-mentioned, detected position or contour of the lesion BYH. The trained model that has been trained on the resection range is used for the estimation. That is, the trained model has been trained with, as training data, the captured image of the lesion and annotation information obtained by addition of an annotation of the resection range to the image by the expert such as the doctor. The image generation section 213 displays the resection range SJH estimated by the support information generation section 214 on the display image IMG3. As described above, the position or contour of the lesion BYH and the resection range SJH are displayed on the display image IMG3 as the support information.

The doctor or the like who uses the endoscope apparatus 1 can determine the resection range SJH with reference to the display image IMG3 on which the lesion BYH and the resection range SJH are displayed. As the method of resecting the lesion using the endoscope, for example, endoscopic submucosal dissection (ESD) can be assumed. In this method, marking is performed on the outer periphery of the resection range. At the time of performing the marking, it is possible to refer to the resection range SJH displayed on the display image IMG3.

7. Seventh Embodiment

In a seventh embodiment, the treatment support mode is a bleeding point recognition mode to automatically recognize a bleeding point. The bleeding point recognition mode is used when bleeding stopping treatment is performed. For example, the bleeding point recognition mode is selected based on input from the operation section 600. Alternatively, a transition from the presence diagnosis mode to the bleeding diagnosis mode may be automatically made. For example, the trained model used in the presence diagnosis mode has been trained on the image in which a bleeding region such as a puddle of blood exists. When the submucosal layer is dissected in the above-mentioned ESD, a puddle of blood is generated in a recess portion after the dissection. Training may be executed with such an image as the training data. With this configuration, the transition from the presence diagnosis mode to the bleeding diagnosis mode may be automatically made when the puddle of blood is generated in the image in the ESD.

Figure 20:
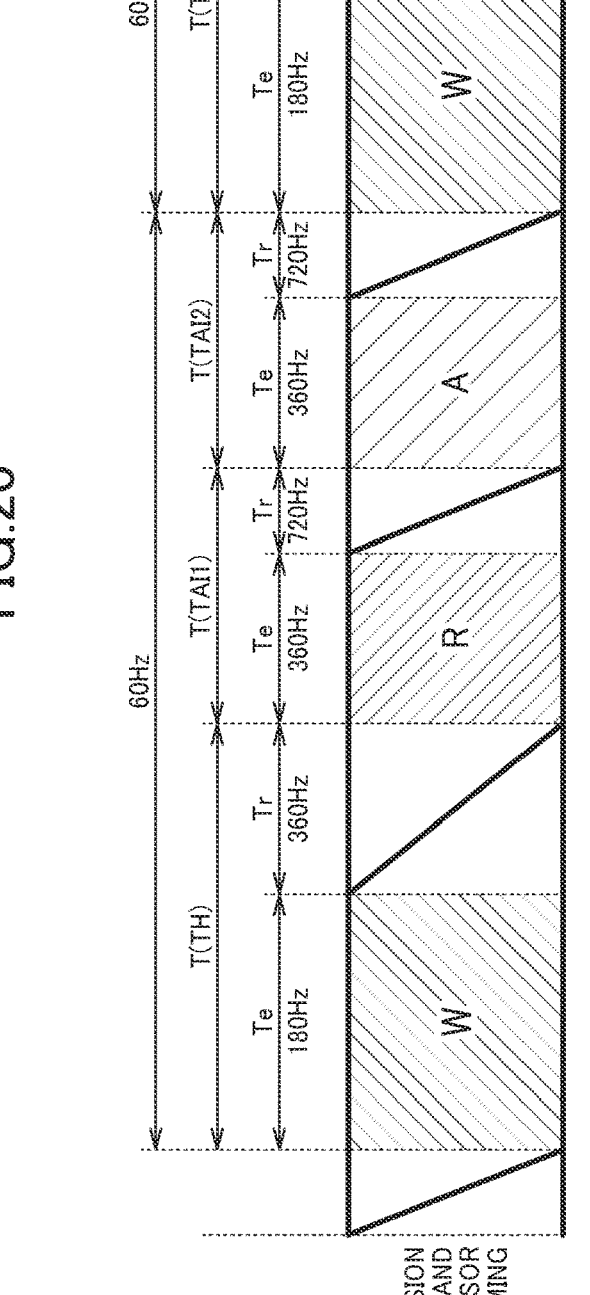
FIG. 20 is a chart showing a light emission sequence and an imaging sequence in a bleeding point recognition mode.

FIG. 20 is a diagram showing a light emission sequence and an imaging sequence in the bleeding point recognition mode. Note that a description about contents that are identical to those in FIG. 16 or the like are omitted.

The light source control section 212 causes the light source section 240 to emit the red light R therefrom in the exposure period Te in the period TAI1, and causes the light source section 240 to emit the amber light A therefrom in the exposure period Te in the period TAI2. The order of emission of the red light R and the amber light A may be reversed.

Figure 21:
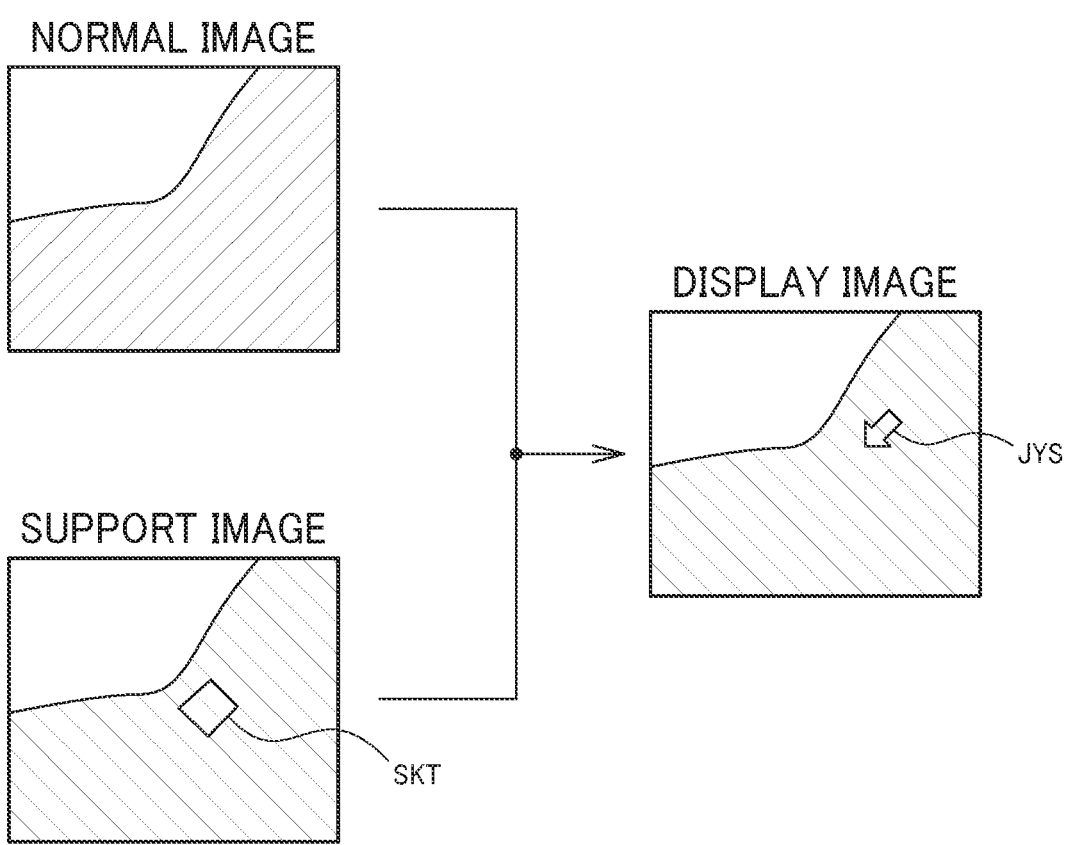
FIG. 21 shows an example of a display image in the bleeding point recognition mode.

FIG. 21 shows an example of a display image in the bleeding point recognition mode. The puddle of blood in the normal image, which is a white light image, is seen in red, dark red, or the like. The hatched portion indicates the puddle of blood. The bleeding point exists on the bottom of the puddle of blood. In a mixed state of blood and water caused by water supply from the air supply/water supply tube, a hemoglobin concentration is higher in the vicinity of the bleeding point. However, since contrast between light and dark of hemoglobin is lower with the white light, the bleeding point is hard to visually recognize in the normal image.

In the support image captured with the red light R and the amber light A, the puddle of blood is in orange or the like. Although light in a wavelength region of the red light R is hardly absorbed by hemoglobin, the amber light A with a wavelength of about 600 nm is absorbed by hemoglobin to some extent. For this reason, contrast between light and dark of hemoglobin tends to be higher in the support image. The hemoglobin concentration is higher in a bleeding flow from the bleeding point, and this portion is colored in orange that is darker than that in the perimeter of the portion. In FIG. 21, a region SKT is a region colored in darker orange. The bleeding point can be estimated from the region SKT.

The trained model in the bleeding point recognition mode has been trained on, as training data, an image of the bleeding region captured with the red light R and the amber light A and annotation information obtained by addition of an annotation of the bleeding point to the image by the expert such as the doctor. The support information generation section 214 uses the above-mentioned trained model to detect the position of the bleeding point from the support image in which the puddle of blood and the above-mentioned region SKT are imaged. The position of the bleeding point is the support information in the bleeding point recognition mode. The image generation section 213 displays the detected position of the bleeding point on the display image using, for example, an arrow JYS or the like. The doctor or the like who uses the endoscope apparatus 1 can identify the bleeding point with reference to the arrow JYS or the like displayed on the display image.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

The invention claimed is:

1. A control device comprising
   a processor comprising hardware, the processor being configured to:
   control an image sensor including a plurality of pixels to;
   read out first imaging signals in a first readout period, the first imaging signals being signals from a first quantity of pixels included in the plurality of pixels, the first readout period being a period for readout of the signals from the first quantity of pixels, and
   read out second imaging signals in a second readout period, the second imaging signals being signals from a second quantity of pixels included in the plurality of pixels, the second readout period being a period for readout of the signals from the second quantity of pixels and being shorter than the first readout period, the second quantity being smaller than the first quantity;
   control a light source that emits illumination light toward an object to:
   emit first illumination light in a first exposure period before the first readout period, and
   emit second illumination light in a second exposure period before the second readout period;

generate a display image from the first imaging signals obtained by imaging of the object illuminated with the first illumination light;

generate a support image from the second imaging signals obtained by imaging of the object illuminated with the second illumination light; and generate support information to support diagnosis or treatment based on the support image;

wherein the processor performs, in a first determination mode, generation of first support information to support diagnosis or treatment based on the second imaging signals and switching from the first determination mode to a second determination mode based on the first support information, and performs, in the second determination mode, generation of second support information that is different in content of diagnosis or treatment from the first support information based on the second imaging signals, in the first determination mode, the second quantity of pixels are pixels obtained by decimating some pixels of the first quantity of pixels, and in the second determination mode, when a region in which the first quantity of pixels are located is defined as a first region of the image sensor and a region in which the second quantity of pixels are located is defined as a second region of the image sensor, the second region is a part of the first region.

2. The control device as defined in claim 1, wherein the second quantity of pixels are pixels obtained by decimating some pixels of the first quantity of pixels.

3. The control device as defined in claim 1, wherein the processor is capable of setting a position of the second region in a variable manner.

4. The control device as defined in claim 3, wherein the processor sets the second region at a center of an image.

5. The control device as defined in claim 3, wherein the processor sets a relatively bright region in the image acquired from the first imaging signals or the second imaging signals as the second region.

6. The control device as defined in claim 1, further comprising a light source that emits the first illumination light and the second illumination light, wherein the processor controls the image sensor to set at least the first quantity of pixels at an exposure state in the first exposure period and set at least the second quantity of pixels at the exposure state in the second exposure period.

7. The control device as defined in claim 6, wherein the second illumination light is light having a spectrum that is different from a spectrum of the first illumination light.

8. The control device as defined in claim 6, wherein the first exposure period is longer than the second exposure period.

9. The control device as defined in claim 1, wherein the image sensor is a rolling shutter-type image sensor, and the processor reads out, in the first readout period, the first imaging signals from pixels on a first quantity of horizontal scanning lines included in a plurality of horizontal scanning lines included in the image sensor, and reads out, in the second readout period, the second imaging signals from pixels on a second quantity of horizontal scanning lines included in the plurality of horizontal scanning lines, the second quantity being smaller than the first quantity.

10. The control device as defined in claim 9, wherein the first quantity of horizontal scanning lines are first to n-th horizontal scanning lines as the plurality of horizontal scanning lines where n is an integer of 2 or more, and the second quantity of horizontal scanning line are odd horizontal scanning lines or even horizontal scanning lines included in the first to n-th horizontal scanning lines.

11. The control device as defined in claim 9, wherein the first quantity of horizontal scanning lines are first to n-th horizontal scanning lines as the plurality of horizontal scanning lines where n is an integer of 2 or more, and the second quantity of horizontal scanning line are i+1-th to i+n/2-th horizontal scanning lines included in the first to n-th horizontal scanning lines where i is an integer of 0 or more and n/2 or less.

12. An endoscope apparatus comprising:

the control device as defined in claim 1; and an imaging device including the image sensor.

13. An endoscope apparatus comprising:

an image sensor including a plurality of pixels;

a light source that emits illumination light toward an object; and a processor comprising hardware, the processor being configured to;

control the image sensor to:

read out first imaging signals in a first readout period, the first imaging signals being signals from a first quantity of pixels included in the plurality of pixels, the first readout period being a period for readout of the signals from the first quantity of pixels, and read out second imaging signals in a second readout period, the second imaging signals being signals from a second quantity of pixels included in the plurality of pixels, the second readout period being a period for readout of the signals from the second quantity of pixels and being shorter than the first readout period, the second quantity being smaller than the first quantity, control the light source to:

emit first illumination light in a first exposure period before the first readout period, and emit second illumination light in a second exposure period before the second readout period, generate a display image from the first imaging signals obtained by imaging of the object illuminated with first illumination light, generate a support image from the second imaging signals obtained by imaging of the object illuminated with the second illumination light, and generate support information to support diagnosis or treatment based on the support image;

wherein the processor performs, in a first determination mode, generation of first support information to support diagnosis or treatment based on the second imaging signals and switching from the first determination mode to a second determination mode based on the first support information, and performs, in the second determination mode, generation of second support information that is different in content of diagnosis or treatment from the first support information based on the second imaging signals, in the first determination mode, the second quantity of pixels are pixels obtained by decimating some pixels of the first quantity of pixels, and in the second determination mode, when a region in which the first quantity of pixels are located is defined as a first region of the image sensor and a region in which the second quantity of pixels are located is defined as a second region of the image sensor, the second region is a part of the first region.

14. A control method for an endoscope apparatus, the control method comprising:

controlling an image sensor including a plurality of pixels to:

read out first imaging signals in a first readout period, the first imaging signals being signals from a first quantity of pixels included in the plurality of pixels, the first readout period being a period for readout of the signals from the first quantity of pixels, and read out second imaging signals in a second readout period, the second imaging signals being signals from a second quantity of pixels included in the plurality of pixels, the second readout period being a period for readout of the signals from the second quantity of pixels and being shorter than the first readout period, the second quantity being smaller than the first quantity;

controlling a light source that emits illumination light toward an object to emit first illumination light in a first exposure period before the first readout period, and emit second illumination light in a second exposure period before the second readout period;

generating a display image from the first imaging signals obtained by imaging of the object illuminated with the first illumination light;

generating a support image from the second imaging signals obtained by imaging of the object illuminated with the second illumination light; and generating support information to support diagnosis or treatment based on the support image;

in a first determination mode, the method further comprises generating first support information to support diagnosis or treatment based on the second imaging signals and switching from the first determination mode to a second determination mode based on the first support information, and, in the second determination mode, generating second support information that is different in content of diagnosis or treatment from the first support information based on the second imaging signals, wherein in the first determination mode, the second quantity of pixels are pixels obtained by decimating some pixels of the first quantity of pixels, and in the second determination mode, when a region in which the first quantity of pixels are located is defined as a first region of the image sensor and a region in which the second quantity of pixels are located is defined as a second region of the image sensor, the second region is a part of the first region.

\* \* \* \* \*